US012714701B2

(12) United States Patent
Poole et al.

(10) Patent No.: US 12,714,701 B2
(45) **Date of Patent: *Aug. 25, 2026**

(54) ORAL PRODUCT WITH NICOTINE AND ION PAIRING AGENT

(71) Applicant: NICOVENTURES TRADING LIMITED, London (GB)

(72) Inventors: Thomas H. Poole, Winston-Salem, NC (US); Christopher Keller, Advance, NC (US); Brian Michael Keyser, Advance, NC (US); Serban C. Moldoveanu, Winston-Salem, NC (US)

(73) Assignee: NICOVENTURES TRADING LIMITED, London (GB)

( * ) Notice: Subject to any disclaimer, the term of this patent is extended or adjusted under 35 U.S.C. 154(b) by 861 days.

This patent is subject to a terminal disclaimer.

(21) Appl. No.: 17/527,202

(22) Filed: Nov. 16, 2021

(65) Prior Publication Data

US 2022/0071984 A1 Mar. 10, 2022

Related U.S. Application Data

(63) Continuation of application No. PCT/US2020/050219, filed on Sep. 10, 2020, and a (Continued)

(51) Int. Cl.

| | |
|---|---|
| ***A61K 31/465*** | (2006.01) |
| ***A61K 9/00*** | (2006.01) |
| ***A61K 47/12*** | (2006.01) |

(52) U.S. Cl.

CPC .......... *A61K 31/465* (2013.01); *A61K 9/0053* (2013.01); *A61K 47/12* (2013.01); *A61K 9/009* (2013.01)

(58) Field of Classification Search

CPC ......... A24B 13/00; A24B 15/16; A24B 15/30; A24B 15/303; A24B 15/308;

(Continued)

(56) References Cited

U.S. PATENT DOCUMENTS

| | | | |
|---|---|---|---|
| 787,611 | A | 4/1905 | Daniels, Jr. et al. |
| 1,086,306 | A | 2/1914 | Oelenheinz |

(Continued)

FOREIGN PATENT DOCUMENTS

| | | |
|---|---|---|
| AU | 2004/275843 | 4/2008 |
| CN | 105918603 | 9/2016 |

(Continued)

OTHER PUBLICATIONS

Acton et al., Chapter 3: Esterases from “Hydrolases-Advances in Research and Publication,” 2003, p. 160.

(Continued)

*Primary Examiner* — Michael H. Wilson
*Assistant Examiner* — Stephanie Lynn Moore
(74) *Attorney, Agent, or Firm* — WOMBLE BOND DICKINSON (US) LLP; Scott R. Breining

(57) ABSTRACT

The disclosure provides compositions configured for oral use, the compositions including at least one filler, water, a basic amine, and an organic acid, an alkali metal salt of an organic acid, or a combination thereof, wherein the organic acid has a logP value of from about 1.4 to about 8.0. At least a portion of the basic amine is associated with at least a portion of the organic acid or the alkali metal salt thereof. The association is in the form of a basic amine-organic acid salt, an ion pair between the basic amine and a conjugate base of the organic acid, or a combination of both. Further provided are methods for stabilizing a composition configured for oral use and for enhancing a predicted buccal absorption of a composition configured for oral use.

46 Claims, 9 Drawing Sheets

Related U.S. Application Data continuation-in-part of application No. 16/568,034, filed on Sep. 11, 2019, now Pat. No. 12,213,510.

(58) Field of Classification Search

CPC ..... A24B 15/403; A24B 15/302; A24B 15/32; A24B 15/301; A24B 15/243; A24B 15/385; A24B 15/42; A24B 15/10; A24B 15/167; A24B 15/281; A24B 15/283; A24B 15/241; A24B 15/246; A24B 15/285; A24B 15/287; A24B 15/34; A24B 15/14; A24B 15/20; A24B 15/245; A24B 15/28; A24B 15/306; A24B 15/38; A24B 3/12; A24B 15/186; A24B 15/24; A24B 15/282; A24B 15/284; A24B 15/406

See application file for complete search history.

(56) References Cited

U.S. PATENT DOCUMENTS 1,376,586 A 5/1921 Schwartz
1,437,095 A 11/1922 Delling
1,757,477 A 5/1930 Rosenhoch
2,033,909 A 3/1936 Cox et al.
2,122,421 A 7/1938 Hawkinson
2,148,147 A 2/1939 Baier
2,170,107 A 8/1939 Baier
2,274,649 A 3/1942 Baier
2,770,239 A 11/1956 Prats et al.
3,339,558 A 9/1967 Waterbury
3,390,686 A 7/1968 Irby et al.
3,550,598 A 12/1970 McGlumphy et al.
3,612,065 A 10/1971 Rosen
3,685,521 A 8/1972 Dock
3,851,653 A 12/1974 Rosen
3,889,689 A 6/1975 Rosen
3,901,248 A 8/1975 Lichtneckert et al.
3,916,914 A 11/1975 Brooks et al.
3,943,940 A 3/1976 Minami
3,943,945 A 3/1976 Rosen
4,143,666 A 3/1979 Rainer
4,144,895 A 3/1979 Fiore
4,148,325 A 4/1979 Solomon et al.
4,150,677 A 4/1979 Osborne, Jr. et al.
4,194,514 A 3/1980 Campbell
4,241,093 A 12/1980 Farag et al.
4,267,847 A 5/1981 Reid
4,289,147 A 9/1981 Wildman et al.
4,340,073 A 7/1982 de la Burde et al.
4,351,346 A 9/1982 Brummer et al.
4,359,059 A 11/1982 Brummer et al.
4,366,823 A 1/1983 Rainer et al.
4,366,824 A 1/1983 Rainer et al.
4,388,933 A 6/1983 Rainer et al.
4,506,682 A 3/1985 Muller
4,513,756 A 4/1985 Pittman et al.
4,528,993 A 7/1985 Sensabaugh, Jr. et al.
4,589,428 A 5/1986 Keritsis
4,605,016 A 8/1986 Soga et al.
4,624,269 A 11/1986 Story et al.
4,641,667 A 2/1987 Schmekel et al.
4,660,577 A 4/1987 Sensabaugh et al.
4,716,911 A 1/1988 Poulose et al.
4,725,440 A 2/1988 Ridgway et al.
4,727,889 A 3/1988 Niven, Jr. et al.
4,737,323 A 4/1988 Martin et al.
4,887,618 A 12/1989 Bernasek et al.
4,889,144 A 12/1989 Tateno et al.
4,941,484 A 7/1990 Clapp et al.
4,967,771 A 11/1990 Fagg et al.
4,986,286 A 1/1991 Roberts et al.
4,987,907 A 1/1991 Townsend
4,991,599 A 2/1991 Tibbetts
4,997,654 A 3/1991 Corsello et al.
5,004,595 A 4/1991 Cherukuri et al.
5,005,593 A 4/1991 Fagg et al.
5,018,540 A 5/1991 Grubbs et al.
5,060,669 A 10/1991 White et al.
5,065,775 A 11/1991 Fagg
5,074,319 A 12/1991 White et al.
5,092,352 A 3/1992 Sprinkle, III et al.
5,099,862 A 3/1992 White et al.
5,121,757 A 6/1992 White et al.
5,131,414 A 7/1992 Fagg
5,131,415 A 7/1992 Munoz et al.
5,148,819 A 9/1992 Fagg
5,167,244 A 12/1992 Kjerstad
5,197,494 A 3/1993 Kramer
5,223,185 A 6/1993 Takei et al.
5,230,354 A 7/1993 Smith et al.
5,234,008 A 8/1993 Fagg
5,243,999 A 9/1993 Smith
5,259,403 A 11/1993 Guy et al.
5,292,528 A 3/1994 Mori et al.
5,301,694 A 4/1994 Raymond et al.
5,318,050 A 6/1994 Gonzalez-Parra et al.
5,343,879 A 9/1994 Teague
5,360,022 A 11/1994 Newton
5,387,093 A 2/1995 Takei et al.
5,387,416 A 2/1995 White et al.
5,417,229 A 5/1995 Summers et al.
5,435,325 A 7/1995 Clapp et al.
5,445,169 A 8/1995 Brinkley et al.
5,472,002 A 12/1995 Covarrubias
5,525,351 A 6/1996 Dam
5,539,093 A 7/1996 Fitzmaurice et al.
5,668,295 A 9/1997 Wahab et al.
5,690,990 A 11/1997 Bonner
5,705,624 A 1/1998 Fitzmaurice et al.
5,713,376 A 2/1998 Berger
5,759,599 A 6/1998 Wampler et al.
5,811,126 A 9/1998 Krishnamurthy
5,844,119 A 12/1998 Weigl
5,882,680 A 3/1999 Suzuki et al.
5,908,032 A 6/1999 Poindexter et al.
6,039,901 A 3/2000 Soper et al.
6,045,835 A 4/2000 Soper et al.
6,056,992 A 5/2000 Lew
6,060,078 A 5/2000 Lee
6,077,524 A 6/2000 Bolder et al.
6,106,875 A 8/2000 Soper et al.
6,117,455 A 9/2000 Takada et al.
6,131,584 A 10/2000 Lauterbach
6,138,683 A 10/2000 Hersh et al.
6,261,589 B1 7/2001 Pearson et al.
6,298,859 B1 10/2001 Kierulff et al.
6,325,859 B1 12/2001 DeRoos et al.
6,482,433 B1 11/2002 DeRoos et al.
6,510,855 B1 1/2003 Korte et al.
6,596,298 B2 7/2003 Leung et al.
6,612,429 B2 9/2003 Dennen
6,631,722 B2 10/2003 MacAdam et al.
6,668,839 B2 12/2003 Williams
6,719,933 B2 4/2004 Nakamura et al.
6,730,832 B1 5/2004 Dominguez et al.
6,772,767 B2 8/2004 Mua et al.
6,834,654 B2 12/2004 Williams
6,845,777 B2 1/2005 Pera
6,887,307 B1 5/2005 Scott et al.
6,895,974 B2 5/2005 Peele
6,923,981 B2 8/2005 Leung et al.
6,929,814 B2 8/2005 Bouwmeesters et al.
6,949,256 B2 9/2005 Fonkwe et al.
6,953,040 B2 10/2005 Atchley et al.
6,958,143 B2 10/2005 Choi et al.
7,014,039 B2 3/2006 Henson et al.
7,025,066 B2 4/2006 Lawson et al.
7,032,601 B2 4/2006 Atchley et al.
7,056,541 B1 6/2006 Stahl et al.
7,067,150 B2 6/2006 Farber et al.
7,115,085 B2 10/2006 Deal
7,173,170 B2 2/2007 Liu et al.
7,208,659 B2 4/2007 Colliver et al.
7,230,160 B2 6/2007 Benning et al.

(56) References Cited

U.S. PATENT DOCUMENTS 7,337,782 B2 3/2008 Thompson
7,494,669 B2 2/2009 Ni et al.
7,507,427 B2 3/2009 Andersen et al.
D592,956 S 5/2009 Thiellier
7,531,192 B2 5/2009 Farber et al.
7,537,110 B2 5/2009 Kutsch et al.
D594,154 S 6/2009 Patel
7,556,047 B2 7/2009 Poindexter et al.
7,584,843 B2 9/2009 Kutsch et al.
7,650,892 B1 1/2010 Groves et al.
7,694,686 B2 4/2010 Atchley et al.
7,798,153 B2 9/2010 Lawrence, Jr. et al.
D625,178 S 10/2010 Bailey et al.
7,810,507 B2 10/2010 Dube et al.
7,833,555 B2 11/2010 Andersen et al.
7,861,728 B2 1/2011 Holton, Jr. et al.
7,900,637 B2 3/2011 Fagerstrom et al.
7,946,295 B2 5/2011 Brinkley et al.
7,950,399 B2 5/2011 Winterson et al.
8,061,362 B2 11/2011 Mua et al.
8,069,861 B2 12/2011 Sinclair, Jr.
8,124,147 B2 2/2012 Cheng et al.
8,186,360 B2 5/2012 Marshall et al.
8,293,295 B2 10/2012 Andersen et al.
8,336,557 B2 12/2012 Kumar et al.
8,343,532 B2 1/2013 Dam et al.
8,397,945 B2 3/2013 Gelardi et al.
8,424,541 B2 4/2013 Crawford et al.
8,434,496 B2 5/2013 Chen et al.
8,469,036 B2 6/2013 Williams et al.
8,469,037 B2 6/2013 Liu et al.
8,529,875 B2 9/2013 Andersen
8,529,914 B2 9/2013 Fuisz et al.
8,545,870 B2 10/2013 Dupinay et al.
8,591,967 B2 11/2013 Andersen et al.
8,613,285 B2 12/2013 Fuisz
8,627,828 B2 1/2014 Strickland et al.
8,642,016 B2 2/2014 Chau et al.
8,714,163 B2 5/2014 Kumar et al.
8,741,348 B2 6/2014 Hansson et al.
8,747,562 B2 6/2014 Mishra et al.
8,828,361 B2 9/2014 Anderson
8,833,378 B2 9/2014 Axelsson et al.
8,846,075 B2 9/2014 Johnson et al.
8,858,984 B2 10/2014 Dam et al.
8,863,755 B2 10/2014 Zhuang et al.
8,871,243 B2 10/2014 Fankhauser et al.
8,931,493 B2 1/2015 Sebastian et al.
8,944,072 B2 2/2015 Chen et al.
8,945,593 B2 2/2015 LoCoco et al.
8,978,661 B2 3/2015 Atchley et al.
8,991,403 B2 3/2015 Chen et al.
8,992,974 B2 3/2015 McCarty
9,027,567 B2 5/2015 Gee et al.
9,039,839 B2 5/2015 Beeson et al.
9,044,035 B2 6/2015 Jackson et al.
9,084,439 B2 7/2015 Holton, Jr.
9,155,321 B2 10/2015 Cantrell et al.
9,155,772 B2 10/2015 Gao et al.
9,161,567 B2 10/2015 Shikata et al.
9,161,908 B2 10/2015 Nilsson
9,167,835 B2 10/2015 Sengupta et al.
9,185,931 B2 11/2015 Gao et al.
9,204,667 B2 12/2015 Cantrell et al.
9,237,768 B2 1/2016 Carroll et al.
9,237,769 B2 1/2016 Mua et al.
9,358,296 B2 6/2016 McCarty
9,372,033 B2 6/2016 Lampe et al.
9,375,033 B2 6/2016 Lampe et al.
9,386,800 B2 7/2016 Sebastian et al.
9,402,414 B2 8/2016 Griscik et al.
9,402,809 B2 8/2016 Axelsson et al.
9,402,810 B2 8/2016 Nilsson
9,414,624 B2 8/2016 Carroll et al.
9,420,825 B2 8/2016 Beeson et al.
9,468,233 B2 10/2016 Macko et al.
9,474,303 B2 10/2016 Holton, Jr.
9,521,864 B2 12/2016 Gao et al.
9,565,867 B2 2/2017 Wittorff et al.
9,629,392 B2 4/2017 Holton, Jr.
9,675,102 B2 6/2017 Hunt et al.
9,763,928 B2 9/2017 Duggins et al.
9,775,376 B2 10/2017 Cantrell et al.
9,801,409 B1 10/2017 Smith
9,848,634 B2 12/2017 Fuisz
9,854,830 B2 1/2018 Gao et al.
9,884,015 B2 2/2018 Gao et al.
9,907,748 B2 3/2018 Borschke et al.
9,925,145 B2 3/2018 Hubinette et al.
9,930,909 B2 4/2018 Gao et al.
9,950,858 B2 4/2018 Byrd et al.
9,999,243 B2 6/2018 Gao et al.
10,039,309 B2 8/2018 Carroll et al.
10,045,976 B2 8/2018 Fusco et al.
10,092,715 B2 10/2018 Axelsson et al.
10,130,120 B2 11/2018 Mishra et al.
10,143,230 B2 12/2018 Mishra et al.
10,149,850 B2 12/2018 Mishra et al.
10,172,810 B2 1/2019 McCarty
10,244,786 B2 4/2019 Gao et al.
10,328,023 B2 6/2019 Romanoschi et al.
10,334,873 B2 7/2019 Mishra et al.
10,349,672 B2 7/2019 Gao et al.
10,357,054 B2 7/2019 Marshall et al.
10,369,182 B2 8/2019 Cohen
10,375,984 B2 8/2019 Hernandez Garcia et al.
10,390,557 B2 8/2019 Börjesson et al.
10,426,726 B2 10/2019 Neergaard
10,463,070 B2 11/2019 Carroll et al.
10,517,322 B1 12/2019 Lee
10,532,046 B2 1/2020 Rogers et al.
10,543,205 B2 1/2020 Wittorff et al.
10,881,132 B2 1/2021 Mua et al.
2001/0045215 A1 11/2001 Meyer et al.
2002/0006919 A1 1/2002 Thosar et al.
2003/0070687 A1 4/2003 Atchley et al.
2003/0118628 A1 6/2003 Tutuncu et al.
2003/0224090 A1 12/2003 Pearce et al.
2004/0020503 A1 2/2004 Williams
2004/0118422 A1 6/2004 Lundin et al.
2004/0191322 A1 9/2004 Hansson
2004/0224020 A1 11/2004 Schoenhard
2004/0261807 A1 12/2004 Dube et al.
2005/0061339 A1 3/2005 Hansson et al.
2005/0115580 A1 6/2005 Quinter et al.
2005/0123601 A1 6/2005 Mane et al.
2005/0196437 A1 9/2005 Bednarz et al.
2005/0215571 A1* 9/2005 Romano ................ A61P 39/02 514/259.41
2005/0244521 A1* 11/2005 Strickland ............. A61K 36/81 424/751
2005/0249676 A1 11/2005 Scott et al.
2006/0130861 A1 6/2006 Luan et al.
2006/0144412 A1 7/2006 Mishra et al.
2006/0174901 A1 8/2006 Karles et al.
2006/0191548 A1 8/2006 Strickland et al.
2006/0236434 A1 10/2006 Conkling et al.
2006/0263414 A1 11/2006 Pan et al.
2006/0272663 A1 12/2006 Dube et al.
2007/0012327 A1 1/2007 Karles et al.
2007/0012328 A1 1/2007 Winterson et al.
2007/0031539 A1 2/2007 Calton
2007/0034220 A1* 2/2007 Pandolfino ............ A24B 15/00 131/364
2007/0062549 A1 3/2007 Holton et al.
2007/0082101 A1 4/2007 Weismuller
2007/0092554 A1 4/2007 Lindberg et al.
2007/0095357 A1 5/2007 Besso et al.
2007/0148292 A1 6/2007 Royo et al.
2007/0184093 A1 8/2007 Hang
2007/0186941 A1 8/2007 Holton, Jr. et al.
2007/0186942 A1 8/2007 Strickland et al.
2007/0261707 A1 11/2007 Winterson et al.
2007/0269386 A1 11/2007 Steen et al.

(56) References Cited

U.S. PATENT DOCUMENTS

2008/0029110 A1 2/2008 Dube et al.
2008/0029116 A1 2/2008 Robinson et al.
2008/0081071 A1 4/2008 Sanghvi et al.
2008/0142025 A1 6/2008 Sinclair
2008/0166395 A1 7/2008 Roush
2008/0173317 A1 7/2008 Robinson et al.
2008/0196730 A1 8/2008 Engstrom et al.
2008/0202536 A1 8/2008 Torrence et al.
2008/0209586 A1 8/2008 Neilsen et al.
2008/0233245 A1 9/2008 White et al.
2008/0305216 A1 12/2008 Crawford et al.
2008/0308115 A1 12/2008 Zimmermann
2008/0317911 A1 12/2008 Schleef et al.
2009/0014343 A1 1/2009 Clark et al.
2009/0014450 A1 1/2009 Bjorkholm
2009/0022856 A1 1/2009 Cheng et al.
2009/0023819 A1 1/2009 Axelsson
2009/0025739 A1 1/2009 Brinkley et al.
2009/0053388 A1 2/2009 Powers et al.
2009/0065013 A1 3/2009 Essen et al.
2009/0095313 A1 4/2009 Fuisz
2009/0142443 A1 6/2009 Robinson et al.
2009/0223989 A1 9/2009 Gelardi
2009/0230003 A1 9/2009 Thiellier
2009/0250360 A1 10/2009 Bellamah et al.
2009/0253754 A1 10/2009 Selmin et al.
2009/0263476 A1 10/2009 Jobdevairakkam et al.
2009/0266837 A1 10/2009 Gelardi et al.
2009/0293889 A1 12/2009 Kumar et al.
2009/0293895 A1 12/2009 Axelsson et al.
2009/0301504 A1 12/2009 Worthen et al.
2009/0301505 A1 12/2009 Liu et al.
2010/0004294 A1 1/2010 Axelsson et al.
2010/0018541 A1 1/2010 Gerardi et al.
2010/0061940 A1 3/2010 Axelsson et al.
2010/0084424 A1 4/2010 Gelardi et al.
2010/0126520 A1 5/2010 Clayton
2010/0133140 A1 6/2010 Bailey et al.
2010/0187143 A1 7/2010 Essen et al.
2010/0218779 A1 9/2010 Zhuang et al.
2010/0260690 A1 10/2010 Kristensen et al.
2010/0264157 A1 10/2010 Bailey et al.
2010/0282267 A1 11/2010 Atchley
2010/0291245 A1 11/2010 Gao et al.
2010/0294292 A1 11/2010 Hodin et al.
2010/0300464 A1 12/2010 Gee et al.
2010/0303969 A1 12/2010 Sengupta et al.
2010/0326454 A1 12/2010 Fuisz
2011/0071183 A1 3/2011 Chen et al.
2011/0083680 A1 4/2011 Mishra et al.
2011/0083681 A1 4/2011 Sengupta et al.
2011/0104218 A1 5/2011 Karles et al.
2011/0129517 A1 6/2011 Rudolph et al.
2011/0139164 A1 6/2011 Mua
2011/0168712 A1 7/2011 Bailey et al.
2011/0220130 A1 9/2011 Mua et al.
2011/0223297 A1 9/2011 Corkery et al.
2011/0232662 A1 9/2011 Liu et al.
2011/0236536 A1 9/2011 Mongia
2011/0247640 A1 10/2011 Beeson et al.
2011/0268809 A1 11/2011 Brinkley et al.
2011/0274628 A1 11/2011 Borschke
2011/0288132 A1 11/2011 Lindberg
2011/0303232 A1 12/2011 Williams
2012/0024301 A1 2/2012 Carroll et al.
2012/0031414 A1 2/2012 Atchley et al.
2012/0031415 A1 2/2012 Essen et al.
2012/0031416 A1 2/2012 Atchley et al.
2012/0037175 A1 2/2012 Cantrell et al.
2012/0039981 A1 2/2012 Pedersen et al.
2012/0055494 A1 3/2012 Hunt et al.
2012/0103353 A1 5/2012 Sebastian et al.
2012/0128734 A1 5/2012 Hubinette et al.
2012/0138073 A1 6/2012 Cantrell et al.
2012/0138074 A1 6/2012 Cantrell et al.
2012/0138075 A1 6/2012 Jespersen et al.
2012/0167902 A1 7/2012 Macko et al.
2012/0177818 A1 7/2012 Trivedi et al.
2013/0005831 A1 1/2013 Rajewski et al.
2013/0008458 A1* 1/2013 Okada .................. A24B 15/287 131/352
2013/0074855 A1 3/2013 Holton, Jr. et al.
2013/0074856 A1 3/2013 Holton, Jr. et al.
2013/0078307 A1 3/2013 Holton, Jr. et al.
2013/0098377 A1 4/2013 Borschke et al.
2013/0118512 A1 5/2013 Jackson et al.
2013/0152953 A1 6/2013 Mua et al.
2013/0177646 A1 7/2013 Hugerth et al.
2013/0186416 A1 7/2013 Gao et al.
2013/0186418 A1 7/2013 Gao et al.
2013/0206115 A1 8/2013 Kragh
2013/0206150 A1 8/2013 Duggins et al.
2013/0206153 A1 8/2013 Beeson et al.
2013/0209540 A1 8/2013 Duggins et al.
2013/0251779 A1 9/2013 Svandal et al.
2013/0263870 A1 10/2013 Cantrell et al.
2013/0274296 A1 10/2013 Jackson et al.
2013/0312774 A1 11/2013 Holton, Jr.
2013/0330379 A1 12/2013 Ylipertula et al.
2013/0330417 A1 12/2013 Dong et al.
2013/0340773 A1 12/2013 Sebastian et al.
2014/0017286 A1 1/2014 Nilsson
2014/0130813 A1 5/2014 Strehle
2014/0134115 A1 5/2014 Golas et al.
2014/0154301 A1 6/2014 Chau et al.
2014/0234392 A1 8/2014 Hansson et al.
2014/0255452 A1 9/2014 Reddick et al.
2014/0261472 A1 9/2014 Carroll et al.
2014/0261485 A1 9/2014 Kobai et al.
2014/0271791 A1 9/2014 Mishra et al.
2014/0271946 A1 9/2014 Kobai et al.
2014/0332013 A1 11/2014 Gao et al.
2015/0068544 A1 3/2015 Moldoveanu et al.
2015/0068545 A1 3/2015 Moldoveanu et al.
2015/0071972 A1 3/2015 Holton, Jr. et al.
2015/0096573 A1 4/2015 Gao et al.
2015/0096574 A1 4/2015 Gao et al.
2015/0096575 A1 4/2015 Gao et al.
2015/0096576 A1 4/2015 Gao et al.
2015/0098996 A1 4/2015 Gao et al.
2015/0101627 A1 4/2015 Marshall et al.
2015/0230515 A1 8/2015 Lampe et al.
2015/0231070 A1 8/2015 Huang
2015/0296868 A1 10/2015 Sutton
2015/0344456 A1* 12/2015 Dull ........................ A61P 25/34 514/343
2015/0368368 A1 12/2015 Retsina et al.
2016/0000140 A1 1/2016 Sebastian et al.
2016/0038552 A1 2/2016 Bredesen et al.
2016/0073657 A1 3/2016 Campomanes et al.
2016/0073676 A1 3/2016 Cantrell et al.
2016/0073689 A1 3/2016 Sebastian et al.
2016/0157515 A1 6/2016 Chapman et al.
2016/0165953 A1 6/2016 Goode, Jr.
2016/0166543 A1 6/2016 Joshi et al.
2016/0186377 A1 6/2016 Haldane et al.
2016/0192703 A1 7/2016 Sebastian et al.
2016/0279056 A1 9/2016 Zhao et al.
2016/0303042 A1 10/2016 Yoshimura et al.
2016/0324777 A1 11/2016 Victor et al.
2017/0007594 A1 1/2017 Borschke
2017/0028672 A1 2/2017 Lim et al.
2017/0099868 A1 4/2017 Gao et al.
2017/0157106 A1 6/2017 Rogers et al.
2017/0164651 A1 6/2017 Mua et al.
2017/0165252 A1 6/2017 Mua et al.
2017/0172995 A1 6/2017 Repaka et al.
2017/0209380 A1 7/2017 Ognibene et al.
2017/0216213 A1 8/2017 Ognibene et al.
2017/0239336 A1 8/2017 Zanetti
2017/0258918 A1 9/2017 Rifkin et al.
2017/0258978 A1 9/2017 Bartlett et al.
2017/0280764 A1 10/2017 Sahlen et al.
2017/0312261 A1 11/2017 Changoer et al.

(56) References Cited

U.S. PATENT DOCUMENTS

| | | | | |
|---|---|---|---|---|
| 2017/0318844 | A1 | 11/2017 | Gordon | |
| 2017/0318858 | A1 | 11/2017 | Hodin et al. | |
| 2017/0360078 | A1 | 12/2017 | Mishra et al. | |
| 2018/0014568 | A1 | 1/2018 | Garcia et al. | |
| 2018/0044856 | A1 | 2/2018 | Dhumpa et al. | |
| 2018/0049979 | A1 | 2/2018 | Zhao et al. | |
| 2018/0051002 | A1 | 2/2018 | Dull et al. | |
| 2018/0140007 | A1 | 5/2018 | Aspgren et al. | |
| 2018/0140521 | A1 | 5/2018 | Geonnotti et al. | |
| 2018/0140554 | A1 | 5/2018 | Wittorff | |
| 2018/0153211 | A1 | 6/2018 | Persson | |
| 2018/0235273 | A1 | 8/2018 | Carroll et al. | |
| 2018/0255826 | A1 | 9/2018 | Persson et al. | |
| 2018/0257801 | A1 | 9/2018 | Persson | |
| 2018/0271112 | A1 | 9/2018 | Barkalow et al. | |
| 2018/0338892 | A1 | 11/2018 | Budde et al. | |
| 2019/0008766 | A1 | 1/2019 | Favara et al. | |
| 2019/0083393 | A1 | 3/2019 | Axelsson et al. | |
| 2019/0110514 | A1 | 4/2019 | Vetter | |
| 2019/0124971 | A1 | 5/2019 | Soffe et al. | |
| 2019/0174812 | A1 | 6/2019 | Nielsen et al. | |
| 2019/0175581 | A1 | 6/2019 | Nielsen et al. | |
| 2019/0246686 | A1 | 8/2019 | Zhuang et al. | |
| 2019/0254337 | A1 | 8/2019 | Bjoerkholm | |
| 2019/0255035 | A1 | 8/2019 | Bruun | |
| 2019/0313689 | A1 | 10/2019 | Beeson et al. | |
| 2019/0350862 | A1 | 11/2019 | Wittorff | |
| 2020/0037638 | A1 | 2/2020 | Faraci et al. | |
| 2020/0128870 | A1 | 4/2020 | Hassler et al. | |
| 2020/0138706 | A1 | 5/2020 | Rudraraju et al. | |
| 2020/0138783 | A1 | 5/2020 | Rinaldi | |
| 2020/0275689 | A1 | 9/2020 | Lewerenz | |
| 2020/0297026 | A1 | 9/2020 | Kannisto et al. | |
| 2020/0305496 | A1 | 10/2020 | Gessesse | |
| 2020/0315241 | A1 | 10/2020 | Rubenstein | |
| 2020/0383373 | A1 | 12/2020 | Stahl et al. | |
| 2021/0023046 | A1 | 1/2021 | Bruun | |
| 2021/0068446 | A1 | 3/2021 | Keller et al. | |
| 2022/0225659 | A1 | 7/2022 | Gessesse et al. | |
| 2022/0295858 | A1 | 9/2022 | Holton, Jr. et al. | |
| 2022/0354785 | A1* | 11/2022 | Sievert .................. | A24B 13/00 |
| 2023/0138306 | A1* | 5/2023 | Zawadzki ............. | A23G 3/364<br>514/343 |

FOREIGN PATENT DOCUMENTS

| | | | |
|---|---|---|---|
| EP | 2177213 | A1 | 4/2010 |
| EP | 2640204 | | 9/2013 |
| EP | 1951074 | B1 | 7/2014 |
| EP | 2804498 | | 11/2014 |
| EP | 2891408 | | 7/2015 |
| SE | 1750488 | | 10/2018 |
| WO | 2002/083177 | A1 | 10/2002 |
| WO | WO 2002/080707 | | 10/2002 |
| WO | WO 2007/053098 | | 5/2007 |
| WO | WO 2007/126361 | | 11/2007 |
| WO | WO 2011/117740 | | 9/2011 |
| WO | WO 2013/119760 | | 8/2013 |
| WO | WO 2013/119799 | | 8/2013 |
| WO | WO 2015/051308 | | 4/2015 |
| WO | WO 2015/067372 | | 5/2015 |
| WO | WO 2015/075745 | | 5/2015 |
| WO | WO 2015/160842 | | 10/2015 |
| WO | WO 2016/075371 | | 5/2016 |
| WO | WO 2016/164470 | | 10/2016 |
| WO | WO 2018/083114 | | 5/2018 |
| WO | WO 2021/086367 | | 5/2021 |

OTHER PUBLICATIONS

Cash, M.J. et al., "Cellulose Derivatives," Imelson, Alan, Food Stabilisers, Thickeners and Gelling Agents, 2010, Blackwell Publishing Ltd., 1st Edition, p. 95-113.

Ester, Valerate, "Chemical Entities of Biological Interest," European Molecular Biology Laboratory, 2019, https://www.ebi.ac.uk/chebi/searchId.do?chebiId=CHEBI:50871.

Fernandes et al., "Manufacture and Characterization of Mucoadhesive Buccal Films Based on Pectin and Gellan Gum Containing Triamcinolone Acetonide," *International Journal of Polymer Science*, vol. 2018, pp. 1-10.

Friedman et al., "Cinnamaldehyde Content in Foods Determined by Gas Chromatography—Mass Spectrometry," 2000, Journal of Agricultural and Food Chemistry, vol. 48, No. 11, pp. 5702-5709.

Guntert in Takeoka, et al., "Flavor Chemistry of Peppermint Oil (*Mentha piperita* L.)," Aroma Active Compounds in Foods ACS Symposium Series; American Chemical Society: Washington, DC 2001.

Lee et al., "Gums, Jellies and Pastilles," in Sugar Confectionery and Chocolate Manufacture, 1973, pp. 226-255.

Niesz, Krisztian, et al., "Sol-gel Synthesis of ordered mesoporous alumina," Chem. Commun., 2005, pp. 1986-1987.

Onal et al., "Some Physicochemical Properties Of The White Sepiolite Known As Pipestone From Kskisehir, Turkey," 2008, Clays and Clay Minerals, vol. 56, No. 5, pp. 511-519.

Szel, et al., "Anti-irritant and anti-inflammatory effects of glycerol and xylitol in sodium lauryl sulphate-induced acute irritation," The Journal of European Academy of Dermatology and Venereology, vol. 29, Issue 12, Dec. 2015, 2333-2341.

Umashankar et al., Chewable Lozenges Formulation a Review, International Research Journal of Pharmacy, 2016, 7(4), 9-16.

V2 Cigs UK, "What is Synthetic Nicotine and is it safe?" Sep. 11, 2019, (https://www.buyv2cigs.co.uk/).

* cited by examiner

Partitioning With 1:1 Nicotine:Counterion (100 ppm)
ppm nicotine in octanol
0
1
2
3
4
5
6
7
8
9
10
Control
NaSO3Hept
Tartaric
Levulinic
Benzoic
Citric
Counterion

ORAL PRODUCT WITH NICOTINE AND ION PAIRING AGENT

CROSS-REFERENCE TO RELATED APPLICATIONS

This application is a continuation of International Application No. PCT/US2020/050219, filed Sep. 10, 2020, and is a continuation-in-part of U.S. application Ser. No. 16/568,034, filed Sep. 11, 2019, each of which is incorporated herein by reference in their entirety and for all purposes.

FIELD OF THE DISCLOSURE

The present disclosure relates to compositions intended for human use. The compositions are adapted for oral use and deliver substances such as nicotine, flavors, and/or active ingredients during use. Such compositions may include tobacco or a product derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

BRIEF SUMMARY

The present disclosure generally provides compositions configured for oral use. The compositions comprise one or more fillers, water; an organic acid or salt thereof, and a basic amine. The organic acid has a log P value of from about 0 to about 8, and the basic amine and at least a portion of the organic acid or salt thereof are present in the form of a salt.

Oral nicotine products are used by placing a nicotine containing matrix between the cheek and the gum. Nicotine is then released from the product and absorbed through the oral mucosa, thereby entering the blood stream where it is circulated systemically. Flavor stability and positive sensory attributes are important elements to a consumer-acceptable oral nicotine product. The organoleptic impact of flavors has been shown to be particularly sensitive to product pH. When the product pH exceeds ca. 7.0, the visual, aroma, and taste impact of some flavors degrades over time, and nicotine may evaporate from the product. This instability is particularly noticeable for certain flavors such as ethyl vanillin, lime, and cinnamon, which also cause darkening of an otherwise white product over time. However, lowering of pH increases the extent of nicotine present in the protonated form. As a dibasic alkaloid, nicotine is capable of accepting two protons (pyridine ring nitrogen: log Kal=3.41; and pyrrolidine ring nitrogen: log $K_{a2}$=8.02), significantly changing the polarity. The overall polarity of nicotine increases from log(P)=1.09 (unprotonated nicotine) to −2.07 (for nicotine protonated on the pyrrolidine ring nitrogen). Passive diffusion of substances such as nicotine across membranes (e.g., mucosal membranes) is a function of molecule polarity and membrane properties, as well as molecular size and ionization (Kokate et al., *PharmSciTech* 2008, 9, 501-504).

Without wishing to be bound by theory, it is believed that downward shift in log(P) as a result of protonation state is the predominant driving force behind the reduction in nicotine absorption with descending pH. (Nair et al., *Journal of Pharmaceutical Sciences* 1997, 86, 257-262; Chen et al., *International Journal of Pharmaceutics* 1999, 184, 63-72; Adrian et al., *International Journal of Pharmaceutics* 2006, 311, 196-202). Specifically, as reported in Adrian et al., while there was still some diffusion across human buccal tissue in a perfusion cell for a nicotine solution at pH=6 (when nicotine is predominantly monoprotonated), the rate was greatly reduced relative a nicotine solution at pH 8.1 (by a factor of ~7).

Surprisingly, it has been found according to the present disclosure that the presence of certain non-polar or lipophilic organic acids or salts thereof enhanced composition stability, and enhanced availability of the nicotine with respect to oral absorption in a composition configured for oral use, relative to a composition configured for oral use which included a polar organic acid. Accordingly, in one aspect, the disclosure provides a composition configured for oral use, the composition comprising: at least one filler; a basic amine; water; and an organic acid, an alkali metal salt of an organic acid, or a combination thereof; wherein the organic acid has a logP value of from about 1.4 to about 8.0, and at least a portion of the basic amine is associated with at least a portion of the organic acid or the alkali metal salt thereof, the association in the form of a basic amine-organic acid salt, an ion pair between the basic amine and a conjugate base of the organic acid, or both.

In some embodiments, the organic acid has a logP value of from about 1.4 to about 4.5. In some embodiments, the organic acid has a logP value of from about 2.5 to about 3.5. In some embodiments, the organic acid has a logP value of from about 4.5 to about 8.0, and wherein the composition further comprises a solubility enhancer. In some embodiments, the solubility enhancer is glycerol or propylene glycol In some embodiments, the composition comprises from about 0.05, about 0.1, about 1, about 1.5, about 2, or about 5, to about 10, about 15, or about 20 molar equivalents of the organic acid, the alkali metal salt thereof, or the combination thereof, relative to the basic amine, calculated as amine free base.

In some embodiments, the composition comprises from about 0.05, about 0.1, about 1, about 1.5, about 2, or about 5, to about 10, about 15, or about 20 molar equivalents of the organic acid, the alkali metal salt thereof, or the combination thereof, relative to the nicotine component, calculated as free base nicotine. In some embodiments, the composition comprises from about 2 to about 10 molar equivalents of the organic acid, the alkali metal salt thereof, or the combination thereof, relative to the nicotine component, calculated as free base nicotine.

In some embodiments, the organic acid is an alkyl carboxylic acid, an aryl carboxylic acid, an alkyl sulfonic acid, an aryl sulfonic acid, or a combination of any thereof.

In some embodiments, the organic acid is octanoic acid, decanoic acid, benzoic acid, heptanesulfonic acid, or a combination thereof. In some embodiments, the organic acid is octanoic acid. In some embodiments, the alkali metal is sodium or potassium.

In some embodiments, the composition comprises the organic acid and a sodium salt of the organic acid. In some embodiments, a ratio of the organic acid to the sodium salt of the organic acid is from about 0.1 to about 10.

In some embodiments, the composition comprises benzoic acid and sodium benzoate, octanoic acid and sodium octanoate, decanoic acid and sodium decanoate, or a combination thereof.

In some embodiments, the pH of the composition is from about 4.0 to about 9.0. In some embodiments, the pH of the composition is from about 4.5 to about 7. In some embodiments, the pH of the composition is from about 5.5 to about 7. In some embodiments, wherein the pH of the composition is from about 4.0 to about 5.5. In some embodiments, the pH of the composition is from about 7.0 to about 9.0.

In some embodiments, the basic amine is nicotine. In some embodiments, the nicotine is present in an amount of from about 0.001 to about 10% by weight of the composition, calculated as the free base and based on the total weight of the composition.

In some embodiments, the at least one filler comprises a cellulose material. In some embodiments, the cellulose material comprises microcrystalline cellulose. In some embodiments, the at least one filler further comprises a cellulose derivative in an amount by weight of from about 1% to about 3%, based on the total weight of the composition. In some embodiments, the cellulose derivative is hydroxypropylcellulose.

In some embodiments, the composition comprises: from about 10 to about 50% of the at least one filler; and from about 5 to about 60% by weight of water, based on the total weight of the composition.

In some embodiments, the composition further comprises one or more active ingredients, one or more flavoring agents, one or more salts, one or more sweeteners, one or more binding agents, one or more humectants, one or more gums, a tobacco material, or combinations thereof.

In some embodiments, the composition further comprises one or more active ingredients selected from the group consisting of nutraceuticals, botanicals, stimulants, amino acids, vitamins, and cannabinoids.

In some embodiments, the composition comprises no more than about 10% by weight of a tobacco material, excluding any nicotine component present, based on the total weight of the composition. In some embodiments, the composition is free of tobacco material.

In some embodiments, the composition is enclosed in a pouch to form a pouched product, the composition optionally being in a granular form.

In another aspect is provided a method of enhancing the stability of a composition configured for oral use, the stabilized composition comprising: at least one filler; a basic amine; water; and an organic acid, an alkali metal salt of an organic acid, or a combination thereof; wherein the organic acid has a logP value of from about 1.4 to about 8.0, the method comprising: mixing the at least one filler with the water, the basic amine, and the organic acid, the alkali metal salt of an organic acid, or the combination thereof to form the composition, wherein at least a portion of the basic amine is associated with at least a portion of the organic acid or the alkali metal salt thereof, the association in the form of a basic amine-organic acid salt, an ion pair between the basic amine and a conjugate base of the organic acid, or both, wherein the composition has a pH of less than about 8.

In some embodiments, the organic acid has a logP value of from about 1.4 to about 4.5. In some embodiments, the organic acid has a logP value of from about 2.5 to about 3.5. In some embodiments, the organic acid has a logP value of from about 4.5 to about 8.0, the method further comprising adding a solubility enhancer to the composition.

In some embodiments, the method further comprises adjusting the pH of the composition to a pH less than about 7.0, wherein adjusting the pH comprises adding an organic acid, a mineral acid, or both, to the composition, providing the pH of less than about 7.0.

In some embodiments, enhancing the stability comprises reducing the evaporative loss of the basic amine from the composition over a storage period, relative to a composition configured for oral use which has a pH of greater than about 8.

In some embodiments, the storage period is one or more of 1 month, 2 months, 3 months, 4 months, 5 months, 6 months, 9 months, or 1 year after preparation.

In some embodiments, the loss of basic amine is less than about 5% after a storage period of 6 months. In some embodiments, the basic amine is nicotine.

In still another aspect is provided method of enhancing a predicted oral mucosal absorption of basic amine from a composition configured for oral use, the composition comprising: at least one filler; a basic amine; water; and an organic acid, an alkali metal salt of an organic acid, or a combination thereof; wherein the organic acid has a logP value of from about 1.4 to about 8.0, the method comprising: mixing the at least one filler with the water, the basic amine, and the organic acid, the alkali metal salt of an organic acid, or the combination thereof to form the composition, wherein at least a portion of the basic amine is associated with at least a portion of the organic acid or the alkali metal salt thereof, the association in the form of a basic amine-organic acid salt, an ion pair between the basic amine and a conjugate base of the organic acid, or both.

In some embodiments, the organic acid has a logP value of from about 1.4 to about 4.5. In some embodiments, the organic acid has a logP value of from about 2.5 to about 3.5. In some embodiments, the organic acid has a logP value of from about 4.5 to about 8.0, the method further comprising adding a solubility enhancer to the composition.

In some embodiments, the method further comprises adjusting the pH of the composition to a pH from about 4.0 to about 7.0. In some embodiments, adjusting the pH comprises adding a mineral acid to the composition.

In some embodiments, the basic amine is nicotine. In some embodiments, enhancing the predicted oral mucosal absorption comprises increasing the total nicotine % permeated relative to a composition comprising an organic acid, an alkali metal salt of an organic acid, or a combination thereof, wherein the organic acid has a logP value of less than about 1.4.

The disclosure includes, without limitations, the following embodiments.

Embodiment 1: A composition configured for oral use, the composition comprising: at least one filler; a basic amine; water; and an organic acid, an alkali metal salt of an organic acid, or a combination thereof, wherein the organic acid has a logP value of from about 1.4 to about 4.5, or from about 4.5 to about 8.0, and at least a portion of the basic amine is associated with at least a portion of the organic acid or the alkali metal salt thereof, the association in the form of a basic amine-organic acid salt, an ion pair between the basic amine and a conjugate base of the organic acid, or both.

Embodiment 2: The composition of embodiment 1, wherein the organic acid has a logP value from about 1.4 to about 4.5.

Embodiment 3: The composition of embodiment 1 or 2, wherein the organic acid has a logP value from about 2.5 to about 3.5.

Embodiment 4: The composition of embodiment 1, wherein the organic acid has a logP value of from about 4.5 to about 8.0, and wherein the composition further comprises a solubility enhancer.

Embodiment 5: The composition of embodiment 4, wherein the solubility enhancer is glycerol or propylene glycol.

Embodiment 6: The composition of any one of embodiments 1-5, comprising from about 0.05, about 0.1, about 1, about 1.5, about 2, or about 5, to about 10, about 15, or about 20 molar equivalents of the organic acid, the alkali metal salt thereof, or the combination thereof, relative to the nicotine component, calculated as free base nicotine.

Embodiment 7: The composition of any one of embodiments 1-6, comprising from about 2 to about 10 molar equivalents of the organic acid, the alkali metal salt thereof, or the combination thereof, relative to the nicotine component, calculated as free base nicotine.

Embodiment 8: The composition of any one of embodiments 1-7, wherein the organic acid is an alkyl carboxylic acid, an aryl carboxylic acid, an alkyl sulfonic acid, an aryl sulfonic acid, or a combination of any thereof.

Embodiment 9: The composition of any one of embodiments 1-8, wherein the organic acid is octanoic acid, decanoic acid, benzoic acid, heptanesulfonic acid, or a combination thereof.

Embodiment 10: The composition of any one of embodiments 1-9, wherein the organic acid is octanoic acid.

Embodiment 11: The composition of any one of embodiments 1-10, wherein the alkali metal is sodium or potassium.

Embodiment 12: The composition of any one of embodiments 1-11, comprising the organic acid and a sodium salt of the organic acid.

Embodiment 13: The composition of any one of embodiments 1-12, wherein a ratio of the organic acid to the sodium salt of the organic acid is from about 0.1 to about 10.

Embodiment 14: The composition of any one of embodiments 1-13, comprising benzoic acid and sodium benzoate, octanoic acid and sodium octanoate, decanoic acid and sodium decanoate, or a combination thereof.

Embodiment 15: The composition of any one of embodiments 1-14, wherein the pH of the composition is from about 4.0 to about 9.0.

Embodiment 16: The composition of any one of embodiments 1-15, wherein the pH of the composition is from about 4.5 to about 7.

Embodiment 17: The composition of any one of embodiments 1-16, wherein the pH of the composition is from about 5.5 to about 7.

Embodiment 18: The composition of any one of embodiments 1-17, wherein the pH of the composition is from about 4.0 to about 5.5.

Embodiment 19: The composition of any one of embodiments 1-18, wherein the pH of the composition is from about 7.0 to about 9.0.

Embodiment 20: The composition of any one of embodiments 1-19, wherein the basic amine is nicotine.

Embodiment 21: The composition of any one of embodiments 1-20, wherein the nicotine is present in an amount of from about 0.001 to about 10% by weight of the composition, calculated as the free base and based on the total weight of the composition.

Embodiment 22: The composition of any one of embodiments 1-21, wherein the at least one filler comprises a cellulose material.

Embodiment 23: The composition of any one of embodiments 1-22, wherein the cellulose material comprises microcrystalline cellulose.

Embodiment 24: The composition of any one of embodiments 1-23, wherein the at least one filler further comprises a cellulose derivative in an amount by weight of from about 1% to about 3%, based on the total weight of the composition.

Embodiment 25: The composition of any one of embodiments 1-24, wherein the cellulose derivative is hydroxypropylcellulose.

Embodiment 26: The composition of any one of embodiments 1-25, comprising: from about 10 to about 50% of the at least one filler; and from about 5 to about 60% by weight of water, based on the total weight of the composition.

Embodiment 27: The composition of any one of embodiments 1-26, further comprising one or more active ingredients, one or more flavoring agents, one or more salts, one or more sweeteners, one or more binding agents, one or more humectants, one or more gums, a tobacco material, or combinations thereof.

Embodiment 28: The composition of any one of embodiments 1-27, further comprising one or more active ingredients selected from the group consisting of nutraceuticals, botanicals, stimulants, amino acids, vitamins, and cannabinoids.

Embodiment 29: The composition of any one of embodiments 1-28, comprising no more than about 10% by weight of a tobacco material, excluding any nicotine component present, based on the total weight of the composition.

Embodiment 30: The composition of any one of embodiments 1-29, wherein the composition is free of tobacco material.

Embodiment 31: The composition of any one of embodiments 1-30, enclosed in a pouch to form a pouched product, the composition optionally being in a granular form.

Embodiment 32: A method of enhancing the stability of a composition configured for oral use, the stabilized composition comprising: at least one filler; a basic amine; water; and an organic acid, an alkali metal salt of an organic acid, or a combination thereof; wherein the organic acid has a logP value of from about 1.4 to about 8.0, the method comprising: mixing the at least one filler with the water, the basic amine, and the organic acid, the alkali metal salt of an organic acid, or the combination thereof to form the composition, wherein at least a portion of the basic amine is associated with at least a portion of the organic acid or the alkali metal salt thereof, the association in the form of a basic amine-organic acid salt, an ion pair between the basic amine and a conjugate base of the organic acid, or both, wherein the composition has a pH of less than about 8.

Embodiment 33: The method of embodiment 32, wherein the organic acid has a logP value of from about 1.4 to about 4.5.

Embodiment 34: The method of embodiment 32, wherein the organic acid has a logP value of from about 2.5 to about 3.5.

Embodiment 35: The method of embodiment 32, wherein the organic acid has a logP value of from about 4.5 to about 8.0, and wherein the method further comprises adding a solubility enhancer to the composition.

Embodiment 36: The method of any one of embodiments 32-35, further comprising adjusting the pH of the composition to a pH less than about 7.0, wherein adjusting the pH comprises adding an organic acid, a mineral acid, or both, to the composition, providing the pH of less than about 7.0.

Embodiment 37: The method of any one of embodiments 32-36, wherein enhancing the stability comprises reducing the evaporative loss of basic amine from the composition over a storage period, relative to a composition configured for oral use which has a pH of greater than about 8.

Embodiment 38: The method of any one of embodiments 32-37, wherein the storage period is one or more of 1 month, 2 months, 3 months, 4 months, 5 months, 6 months, 9 months, or 1 year after preparation.

Embodiment 39: The method of any one of embodiments 32-38, wherein the basic amine is nicotine.

Embodiment 40: The method of embodiment 39, wherein the loss of nicotine is less than about 5% after a storage period of 6 months.

Embodiment 42: A method of enhancing a predicted oral mucosal absorption of basic amine from a composition configured for oral use, the composition comprising: at least one filler; a basic amine; water; and an organic acid, an alkali metal salt of an organic acid, or a combination thereof; wherein the organic acid has a logP value of from about 1.4 to about 8.0, the method comprising: mixing the at least one filler with the water, the basic amine, and the organic acid, the alkali metal salt of an organic acid, or the combination thereof to form the composition, wherein at least a portion of the basic amine is associated with at least a portion of the organic acid or the alkali metal salt thereof, the association in the form of a basic amine-organic acid salt, an ion pair between the basic amine and a conjugate base of the organic acid, or both.

Embodiment 43: The method of embodiment 42, wherein the organic acid has a logP value of from about 1.4 to about 4.5.

Embodiment 44: The method of embodiment 43, wherein the organic acid has a logP value of from about 2.5 to about 3.5.

Embodiment 45: The method of embodiment 44, wherein the organic acid has a logP value of from about 4.5 to about 8.0, and wherein the method further comprises adding a solubility enhancer to the composition.

Embodiment 46: The method of any one of embodiments 42-45, further comprising adjusting the pH of the composition to a pH from about 4.0 to about 7.0.

Embodiment 47: The method of embodiment 46, wherein adjusting the pH comprises adding a mineral acid to the composition.

Embodiment 48: The method of any one of embodiments 42-47, wherein the basic amine is nicotine.

Embodiment 49: The method of any one of embodiments 42-48, wherein enhancing the predicted buccal absorption comprises increasing the total nicotine % permeated relative to a composition comprising an organic acid, an alkali metal salt of an organic acid, or a combination thereof, wherein the organic acid has a logP value of less than about 1.4.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Having thus described aspects of the disclosure in the foregoing general terms, reference will now be made to the accompanying drawings, which are not necessarily drawn to scale. The drawings are exemplary only, and should not be construed as limiting the disclosure.

Figure 1:
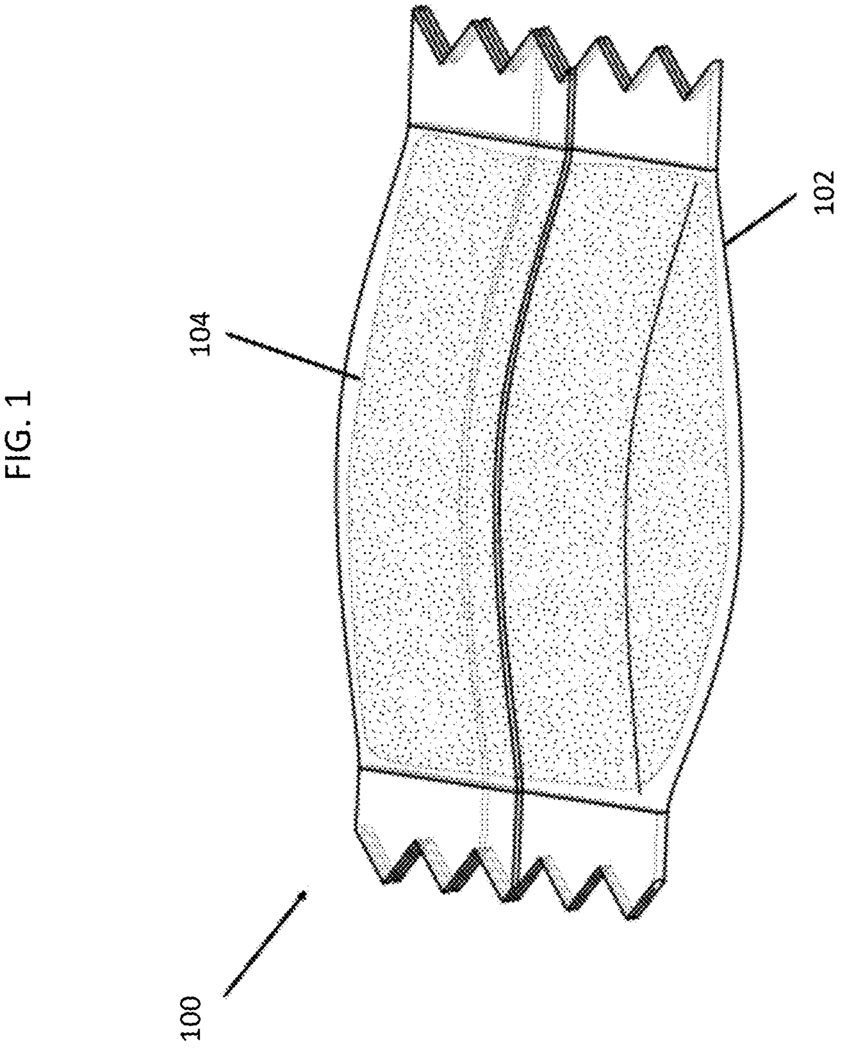
Figure 2:
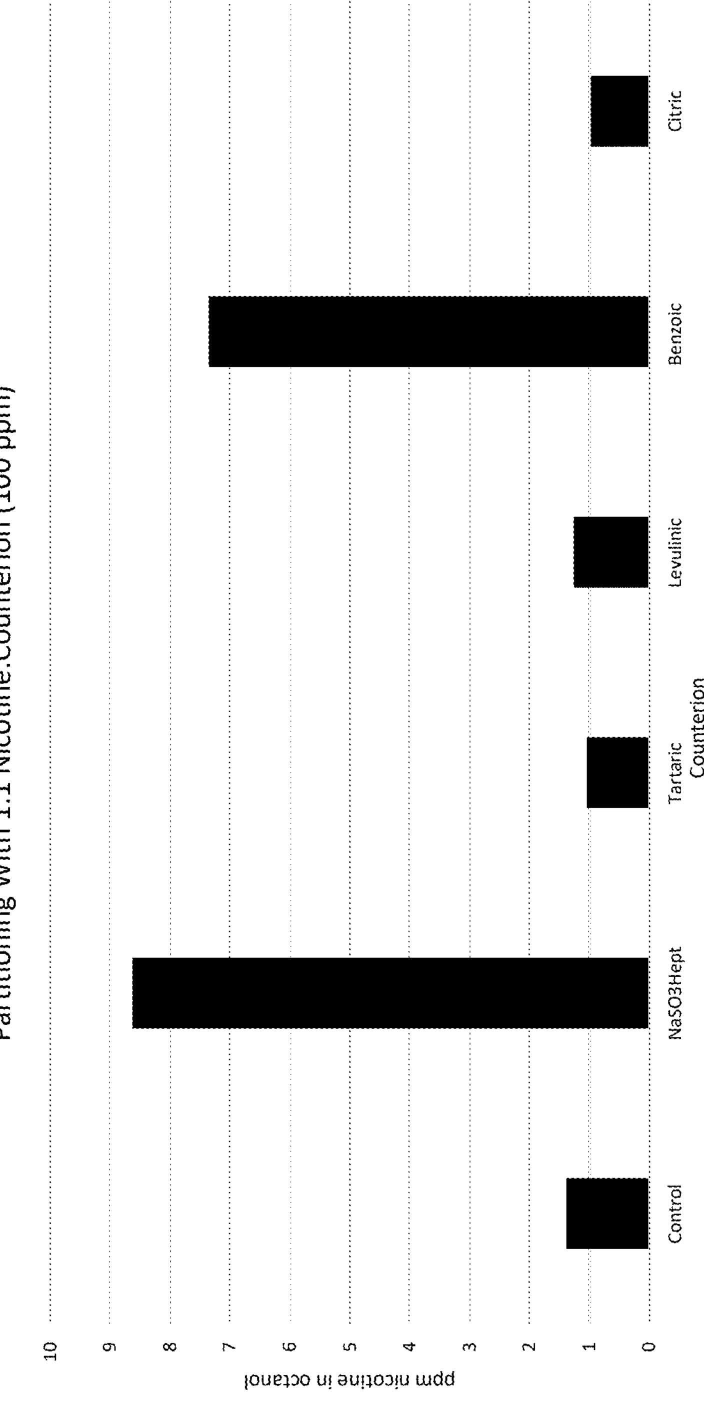
Figure 3:
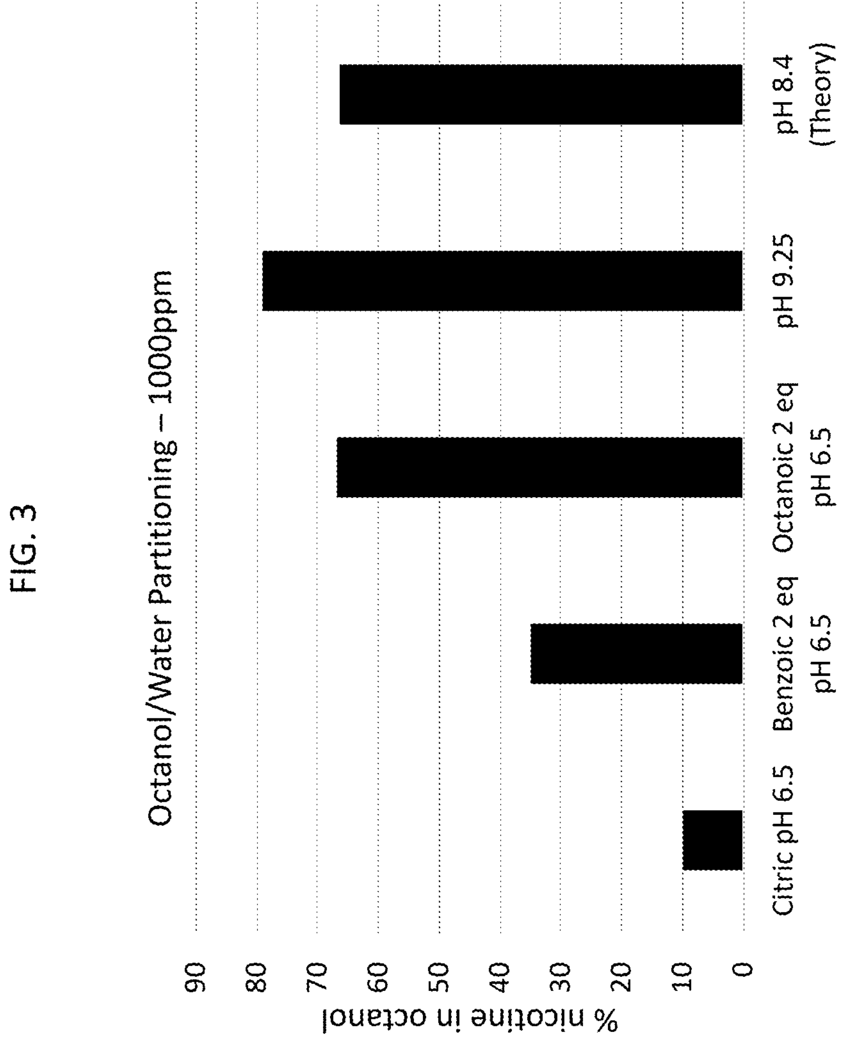
Figure 4:
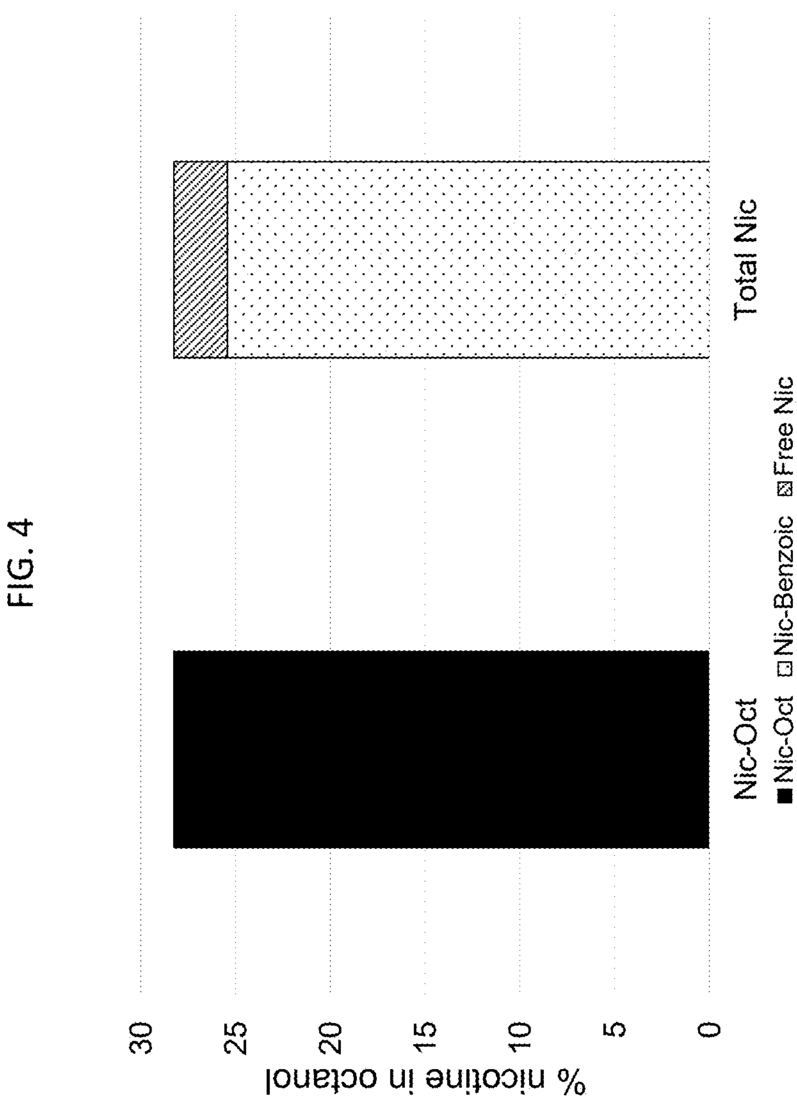
Figure 5:
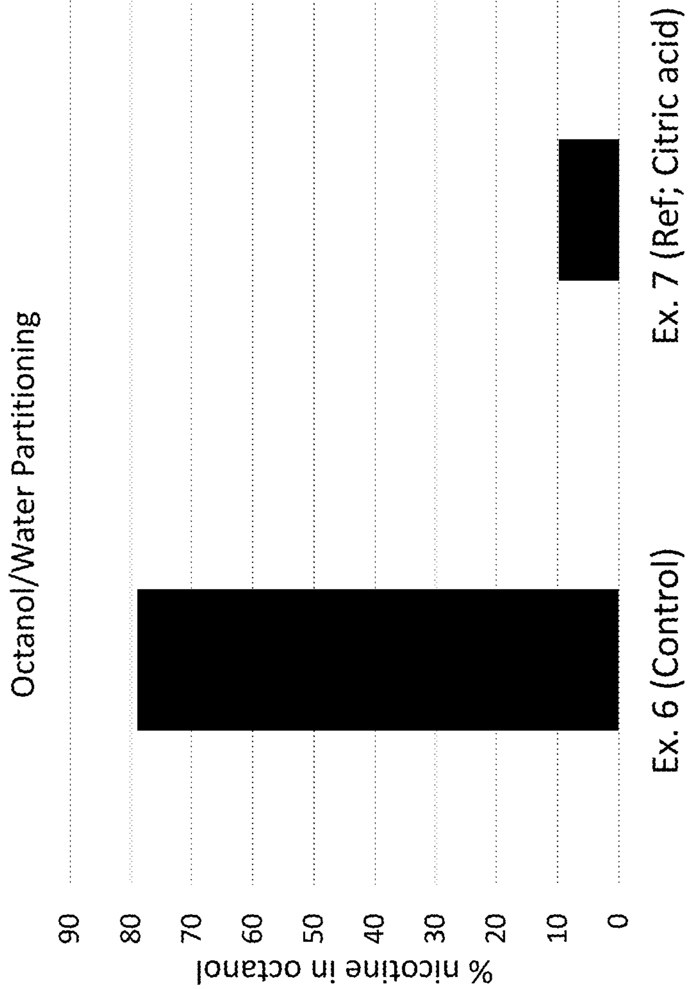
Figure 6:
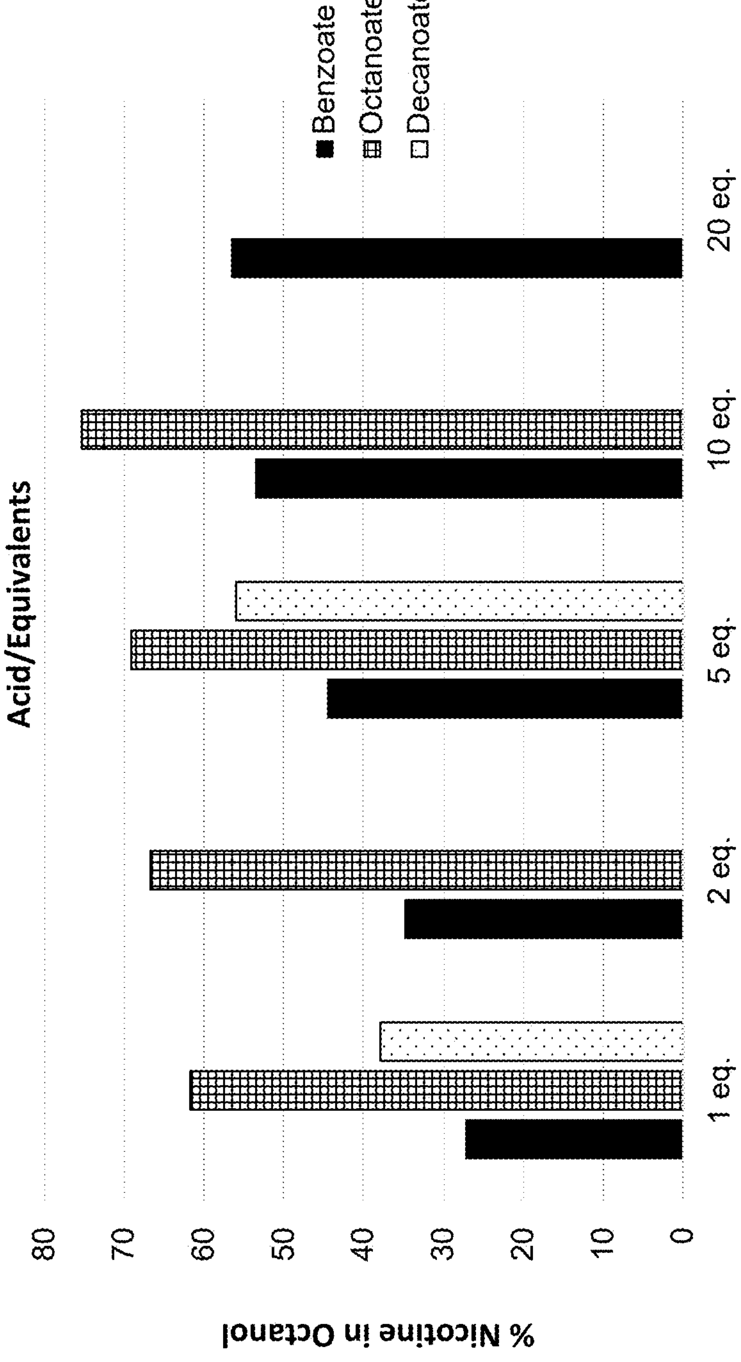
Figure 7:
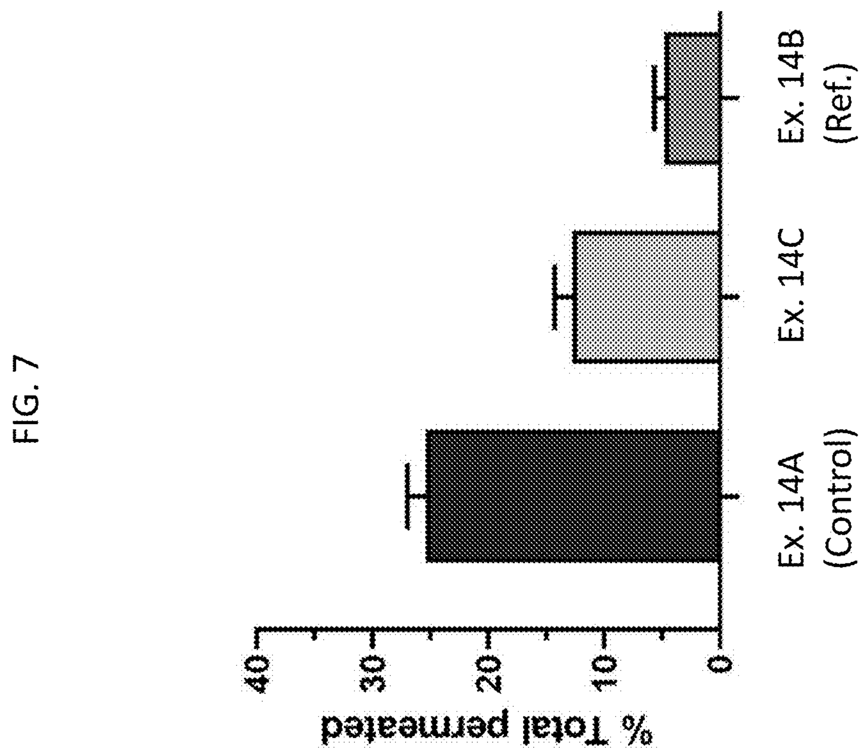
Figure 8:
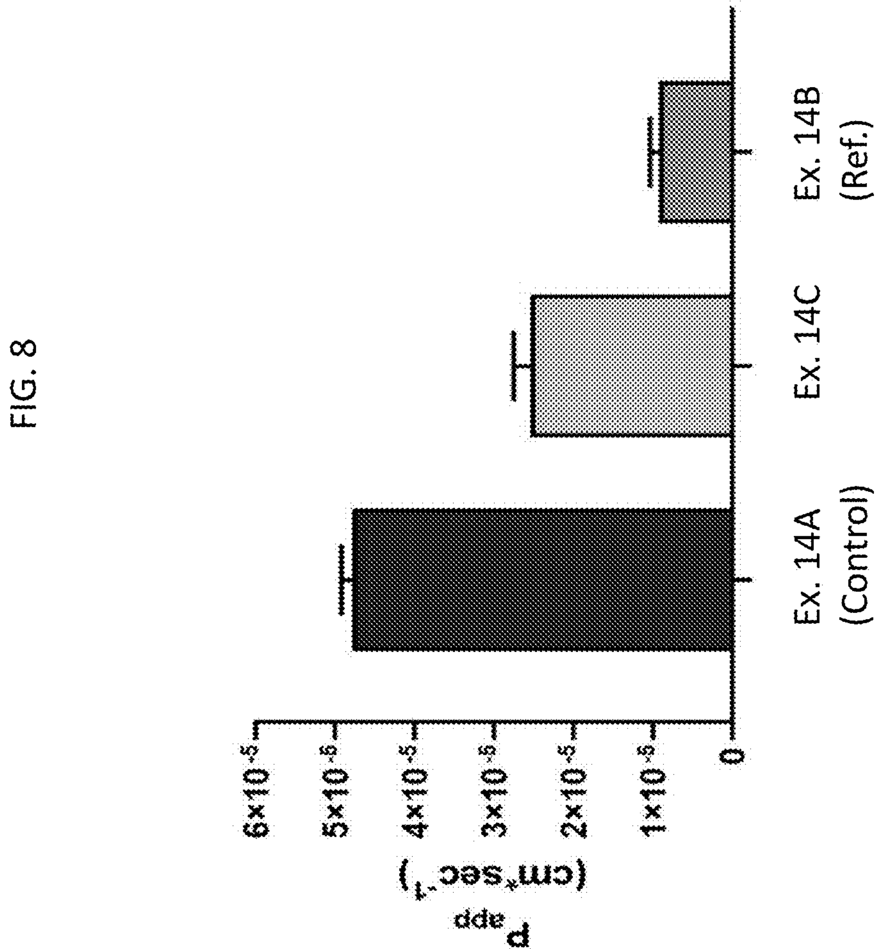
Figure 9:
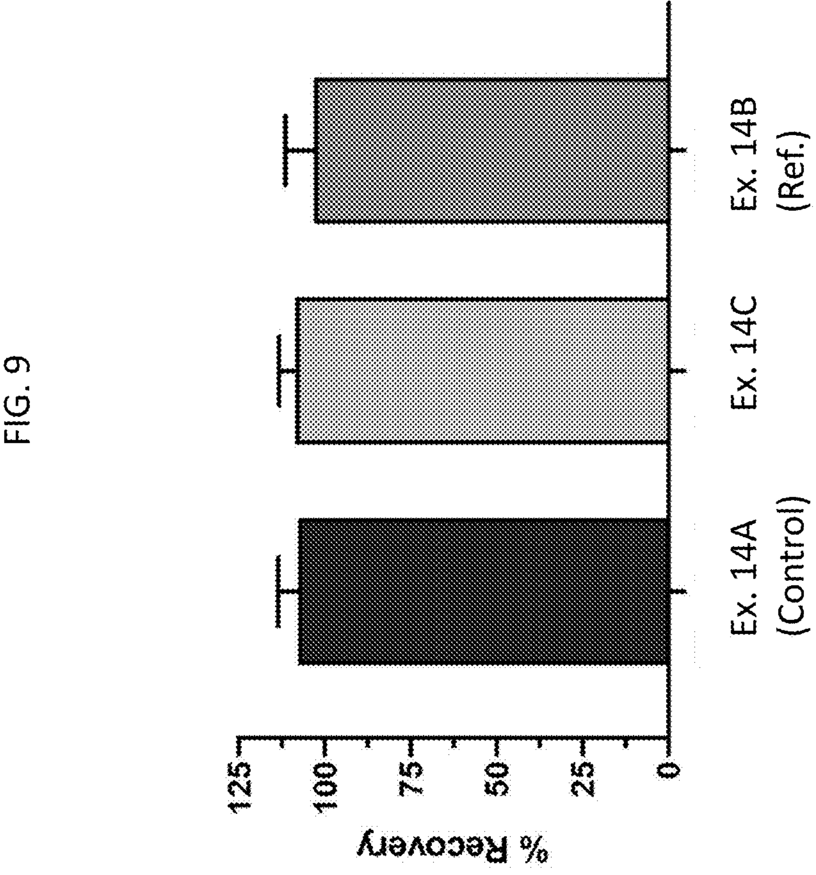

FIG. 1 is a perspective view of a pouched product embodiment according to an example embodiment of the present disclosure including a pouch or fleece at least partially filled with a composition configured for oral use;

FIG. 2 is a bar graph showing octanol-water partitioning of nicotine for embodiments of the disclosure;

FIG. 3 is a bar graph showing octanol-water partitioning of nicotine for embodiments of the disclosure;

FIG. 4 is a bar graph showing octanol-water partitioning of nicotine for an embodiment of the disclosure;

FIG. 5 is a bar graph showing octanol-water partitioning of nicotine for a control and a reference composition;

FIG. 6 is a bar graph showing octanol-water partitioning of nicotine for embodiments of the disclosure with different organic acid salts and concentrations;

FIG. 7 is a bar graph of total % nicotine membrane permeation for an embodiment of the disclosure;

FIG. 8 is a bar graph of nicotine membrane permeation for an embodiment of the disclosure; and FIG. 9 is a bar graph showing percent recovery of nicotine for an embodiment of the disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the mixture including water. Unless otherwise indicated, reference to "weight percent" of a mixture reflects the total wet weight of the mixture (i.e., including water).

For customer satisfaction, it is desirable to provide a basic amine-containing composition configured for oral use which retains the initial basic amine content during storage, and which delivers substantially the full amount of basic amine initially present in the composition. The present disclosure provides compositions which combine a basic amine and a non-polar or lipophilic organic acid salt in an acidic matrix which exhibit enhanced retention of the initial basic amine content during storage, and are predicted to deliver more of the basic amine to the user upon use of the composition, relative to a composition which contains a polar organic acid salt in an acidic matrix (e.g., citric acid or sodium citrate).

In some embodiments, the basic amine is nicotine. Surprisingly, according to the present disclosure, it has been found that in certain embodiments, the presence of a non-polar or lipophilic organic acid salt enhanced composition stability and enhanced membrane permeability of the nicotine in a model system of oral absorption at an acidic pH, relative to a composition configured for oral use which included a polar organic acid salt. The enhanced nicotine permeation is particularly surprising in view of the predicted decrease in permeability associated with nicotine protonation under acidic conditions.

Composition

The composition as disclosed herein comprises at least one filler; a basic amine, such as nicotine or a nicotine component; water; and an organic acid, an alkali metal salt of an organic acid, or a combination thereof, wherein the organic acid has a logP value of from about 1.4 to about 8.0. At least a portion of the basic amine is associated with at least a portion of the organic acid or the alkali metal salt thereof. The association is in the form of a basic amine-organic acid salt, an ion pair between the basic amine and a conjugate base of the organic acid, or both. The relative amounts of the various components within the composition may vary, and typically are selected so as to provide the desired sensory and performance characteristics to the composition. The example individual components of the composition are described further herein below.

Ion Pairing

As disclosed herein, at least a portion of the basic amine is associated with at least a portion of the organic acid or the alkali metal salt thereof. Depending on multiple variables (concentration, pH, nature of the organic acid, and the like), the basic aminepresent in the composition can exist in multiple forms, including ion paired, in solution (i.e., fully solvated), as the free base, as a cation, as a salt, or any combination thereof. In some embodiments, the association between the basic amine and at least a portion of the organic acid or the alkali metal salt thereof is in the form of an ion pair between the basic amine and a conjugate base of the organic acid.

Ion pairing describes the partial association of oppositely charged ions in relatively concentrated solutions to form distinct chemical species called ion pairs. The strength of the association (i.e., the ion pairing) depends on the electrostatic force of attraction between the positive and negative ions (i.e., a protonated basic amine such as nicotine, and the conjugate base of the organic acid). By "conjugate base" is meant the base resulting from deprotonation of the corresponding acid (e.g., benzoate is the conjugate base of benzoic acid). On average, a certain population of these ion pairs exists at any given time, although the formation and dissociation of ion pairs is continuous. In the composition as disclosed herein, and/or upon oral use of said composition (e.g., upon contact with saliva), the basic amine, for example nicotine, and the conjugate base of the organic acid exist at least partially in the form of an ion pair. Without wishing to be bound by theory, it is believed that such ion pairing may minimize chemical degradation of the basic amine and/or enhance the oral availability of the basic amine (e.g., nicotine). At alkaline pH values (e.g., such as from about 7.5 to about 9), certain basic amines, for example nicotine, are largely present in the free base form, which has relatively low water solubility, and low stability with respect to evaporation and oxidative decomposition, but high mucosal availability. Conversely, at acidic pH values (such as from about 6.5 to about 4), certain basic amines, for example nicotine, are largely present in a protonated form, which has relatively high water solubility, and higher stability with respect to evaporation and oxidative decomposition, but low mucosal availability. Surprisingly, according to the present disclosure, it has been found that the properties of stability, solubility, and availability of the nicotine in a composition configured for oral use can be mutually enhanced through ion pairing or salt formation of nicotine with appropriate organic acids and/or their conjugate bases. Specifically, nicotine-organic acid ion pairs of moderate lipophilicity result in favorable stability and absorption properties. Lipophilicity is conveniently measured in terms of logP, the partition coefficient of a molecule between a lipophilic phase and an aqueous phase, usually octanol and water, respectively. An octanol-water partitioning favoring distribution of a basic amine-organic acid ion pair into octanol is predictive of good absorption of the basic amine present in the composition through the oral mucosa.

As noted above, at alkaline pH values (e.g., such as from about 7.5 to about 9), nicotine is largely present in the free base form (and accordingly, a high partitioning into octanol), while at acidic pH values (such as from about 6.5 to about 4), nicotine is largely present in a protonated form (and accordingly, a low partitioning into octanol). Surprisingly, according to the present disclosure, it has been found that an ion pair between certain organic acids (e.g., having a logP value of from about 1.4 to about 8.0. such as from about 1.4 to about 4.5, allows nicotine partitioning into octanol consistent with that predicted for nicotine partitioning into octanol at a pH of 8.4.

One of skill in the art will recognize that the extent of ion pairing in the disclosed composition, both before and during use by the consumer, may vary based on, for example, pH, the nature of the organic acid, the concentration of basic amine, the concentration of the organic acid or conjugate base of the organic acid present in the composition, the moisture content of the composition, the ionic strength of the composition, and the like. One of skill in the art will also recognize that ion pairing is an equilibrium process influenced by the foregoing variables. Accordingly, quantification of the extent of ion pairing is difficult or impossible by calculation or direct observation. However, as disclosed herein, the presence of ion pairing may be demonstrated through surrogate measures such as partitioning of the basic amine between octanol and water or membrane permeation of aqueous solutions of the basic amine plus organic acids and/or their conjugate bases.

Organic Acid

As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($-CO_2H$) or sulfonic acids ($-SO_2OH$). As used herein, reference to organic acid means an organic acid that is intentionally added. In this regard, an organic acid may be intentionally added as a specific composition ingredient as opposed to merely being inherently present as a component of another composition ingredient (e.g., the small amount of organic acid which may inherently be present in a composition ingredient, such as a tobacco material).

Suitable organic acids will typically have a range of lipophilicities (i.e., a polarity giving an appropriate balance of water and organic solubility). Typically, lipophilicities of suitable organic acids, as indicated by logP, will vary between about 1.4 and about 4.5 (more soluble in octanol than in water). In some embodiments, the organic acid has a logP value of from about 1.5 to about 4.0, e.g., from about 1.5, about 2.0, about 2.5, or about 3.0, to about 3.5, about 4.0, about 4.5, or about 5.0. Particularly suitable organic acids have a logP value of from about 1.7 to about 4, such as from about 2.0, about 2.5, or about 3.0, to about 3.5, or about 4.0. In specific embodiments, the organic acid has a logP value of about 2.5 to about 3.5. In some embodiments, organic acids outside this range may also be utilized for various purposes and in various amounts, as described further herein below. For example, in some embodiments, the organic acid may have a logP value of greater than about 4.5, such as from about 4.5 to about 8.0. Particularly, the presence of certain solvents or solubilizing agents (e.g., inclusion in the composition of glycerin or propylene glycol) may extend the range of lipophilicity (i.e., values of logP higher than 4.5, such as from about 4.5 to about 8.0).

Without wishing to be bound by theory, it is believed that moderately lipophilic organic acids (e.g., logP of from about 1.4 to about 4.5) produce ion pairs with nicotine which are of a polarity providing good octanol-water partitioning of the ion pair, and hence partitioning of nicotine, into octanol versus water. As discussed above, such partitioning into octanol is predictive of favorable oral availability. In some embodiments, the organic acid has a log P value of from about 1.4 to about 4.5, such as about 1.5, about 2, about 2.5, about 3, about 3.5, about 4 or about 4.5. In some embodiments, the organic acid has a log P value of from about 2.5 to about 3.5.

In some embodiments, the organic acid is a carboxylic acid or a sulfonic acid. The carboxylic acid or sulfonic acid functional group may be attached to any alkyl, cycloalkyl, heterocycloalkyl, aryl, or heteroaryl group having, for example, from one to twenty carbon atoms ($C_1$-$C_{20}$). In some embodiments, the organic acid is an alkyl, cycloalkyl, heterocycloalkyl, aryl, or heteroaryl carboxylic or sulfonic acid.

As used herein, "alkyl" refers to any straight chain or branched chain hydrocarbon. The alkyl group may be saturated (i.e., having all $sp^3$ carbon atoms), or may be unsaturated (i.e., having at least one site of unsaturation). As used herein, the term "unsaturated" refers to the presence of a carbon-carbon, $sp^2$ double bond in one or more positions within the alkyl group. Unsaturated alkyl groups may be mono- or polyunsaturated. Representative straight chain alkyl groups include, but are not limited to, methyl, ethyl, n-propyl, n-butyl, n-pentyl, and n-hexyl. Branched chain alkyl groups include, but are not limited to, isopropyl, sec-butyl, isobutyl, tert-butyl, isopentyl, and 2-methylbutyl. Representative unsaturated alkyl groups include, but are not limited to, ethylene or vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. An alkyl group can be unsubstituted or substituted.

"Cycloalkyl" as used herein refers to a carbocyclic group, which may be mono- or bicyclic. Cycloalkyl groups include rings having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted, and may include one or more sites of unsaturation (e.g., cyclopentenyl or cyclohexenyl).

The term "aryl" as used herein refers to a carbocyclic aromatic group. Examples of aryl groups include, but are not limited to, phenyl and naphthyl. An aryl group can be unsubstituted or substituted.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl group comprises up to 20 carbon atoms and from 1 to 3 heteroatoms selected from N, O, and S. A heteroaryl or heterocycloalkyl may be a monocycle having 3 to 7 ring members (for example, 2 to 6 carbon atoms and 1 to 3 heteroatoms selected from N, O, and S) or a bicycle having 7 to 10 ring members (for example, 4 to 9 carbon atoms and 1 to 3 heteroatoms selected from N, O, and S), for example: a bicyclo[4,5], [5,5], [5,6], or [6,6] system. Examples of heteroaryl groups include by way of example and not limitation, pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl. Examples of heterocycloalkyls include by way of example and not limitation, dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl. Heteroaryl and heterocycloalkyl groups can be unsubstituted or substituted.

"Substituted" as used herein and as applied to any of the above alkyl, aryl, cycloalkyl, heteroaryl, heterocyclyl, means that one or more hydrogen atoms are each independently replaced with a substituent. Typical substituents include, but are not limited to, —Cl, Br, F, alkyl, —OH, —$OCH_3$, $NH_2$, —$NHCH_3$, —$N(CH_3)_2$, —CN, —NC(═O) $CH_3$, —C(═O)—, —C(═O) $NH_2$, and —C(═O)$N(CH_3)_2$. Wherever a group is described as "optionally substituted," that group can be substituted with one or more of the above substituents, independently selected for each occasion. In some embodiments, the substituent may be one or more methyl groups or one or more hydroxyl groups.

In some embodiments, the organic acid is an alkyl carboxylic acid. Non-limiting examples of alkyl carboxylic acids include formic acid, acetic acid, propionic acid, butyric acid, valeric acid, caproic acid, heptanoic acid, octanoic acid, nonanoic acid, decanoic acid, undecanoic acid, dodecanoic acid, stearic acid, oleic acid, linoleic acid, linolenic acid, and the like.

In some embodiments, the organic acid is an alkyl sulfonic acid. Non-limiting examples of alkyl sulfonic acids include propanesulfonic acid, heptanesulfonic acid, and octanesulfonic acid.

In some embodiments, the alkyl carboxylic or sulfonic acid is substituted with one or more hydroxyl groups. Non-limiting examples include glycolic acid, 4-hydroxybutyric acid, and lactic acid.

In some embodiments, an organic acid may include more than one carboxylic acid group or more than one sulfonic acid group (e.g., two, three, or more carboxylic acid groups). Non-limiting examples include oxalic acid, fumaric acid, maleic acid, and glutaric acid. In organic acids containing multiple carboxylic acids (e.g., from two to four carboxylic acid groups), one or more of the carboxylic acid groups may be esterified. Non-limiting examples include succinic acid monoethyl ester, monomethyl fumarate, monomethyl or dimethyl citrate, and the like.

In some embodiments, the organic acid may include more than one carboxylic acid group and one or more hydroxyl groups. Non-limiting examples of such acids include tartaric acid, citric acid, and the like.

In some embodiments, the organic acid is an aryl carboxylic acid or an aryl sulfonic acid. Non-limiting examples of aryl carboxylic and sulfonic acids include benzoic acid, toluic acids, salicylic acid, benzenesulfonic acid, and p-toluenesulfonic acid.

Further non-limiting examples of organic acids which may be useful in certain embodiments include 2,2-dichloroacetic acid, 2-hydroxyethanesulfonic acid, 2-oxoglutaric acid, 4-acetamidobenzoic acid, 4-aminosalicylic acid, adipic acid, ascorbic acid (L), aspartic acid (L), alpha-methylbutyric acid, camphoric acid (+), camphor-10-sulfonic acid (+), cinnamic acid, cyclamic acid, dodecylsulfuric acid, ethane-1,2-disulfonic acid, ethanesulfonic acid, furoic acid, galactaric acid, gentisic acid, glucoheptonic acid, gluconic acid, glucuronic acid, glutamic acid, glycerophosphoric acid, glycolic acid, hippuric acid, isobutyric acid, isovaleric acid, lactobionic acid, lauric acid, levulinic acid, malic acid, malonic acid, mandelic acid, methanesulfonic acid, naphthalene-1,5-disulfonic acid, naphthalene-2-sulfonic acid, oleic acid, palmitic acid, pamoic acid, phenylacetic acid, pyroglutamic acid, pyruvic acid, sebacic acid, stearic acid, and undecylenic acid.

Examples of suitable acids include, but are not limited to, the list of organic acids in Table 1.

TABLE 1

Non-limiting examples of suitable organic acids

| Acid Name | log(P) |
|---|---|
| benzoic acid | 1.9 |
| phenylacetic | 1.4 |
| p-toluic acid | 2.3 |
| ethyl benzoic acid | 2.9 |
| isopropyl benzoic acid | 3.5 |
| 4-phenylbutyric | 2.4 |
| 2-napthoxyacetic acid | 2.5 |
| napthylacetic acid | 2.7 |
| heptanoic acid | 2.5 |
| octanoic acid | 3.05 |
| nonanoic acid | 3.5 |
| decanoic acid | 4.09 |
| 9-deceneoic acid | 3.3 |
| 2-deceneoic acid | 3.8 |
| 10-undecenoic acid | 3.9 |
| dodecandioic acid | 3.2 |
| dodecanoic acid | 4.6 |
| myristic acid | 5.3 |
| palmitic acid | 6.4 |
| stearic acid | 7.6 |
| cyclohexanebutanoic acid | 3.4 |
| 1-heptanesulfonic acid | 2.0 |
| 1-octanesulfonic acid | 2.5 |
| 1-nonanesulfonic acid | 3.1 |
| monooctyl succinate | 2.8 |

In some embodiments, the organic acid is a mono ester of a di- or poly-acid, such as mono-octyl succinate, mono-octyl fumarate, or the like.

The selection of organic acid may further depend on additional properties in addition to or without consideration to the logP value. For example, an organic acid should be one recognized as safe for human consumption, and which has acceptable flavor, odor, volatility, stability, and the like. Determination of appropriate organic acids is within the purview of one of skill in the art.

In some embodiments, the organic acid is benzoic acid, a toluic acid, benzenesulfonic acid, toluenesulfonic acid, hexanoic acid, heptanoic acid, decanoic acid, or octanoic acid. In some embodiments, the organic acid is benzoic acid, octanoic acid, or decanoic acid. In some embodiments, the organic acid is octanoic acid.

In some embodiments, more than one organic acid may be present. For example, the composition may comprise two, or three, or four, or more organic acids. Accordingly, reference herein to "an organic acid" contemplates mixtures of two or more organic acids. The relative amounts of the multiple organic acids may vary. For example, a composition may comprise equal amounts of two, or three, or more organic acids, or may comprise different relative amounts. In this manner, it is possible to include certain organic acids (e.g., citric acid or myristic acid) which have a logP value outside the desired range, when combined with other organic acids to provide the desired average logP range for the combination. In some embodiments, it may be desirable to include organic acids in the composition which have logP values outside the desired range for purposes such as, but not limited to, providing desirable organoleptic properties, stability, as flavor components, and the like. Further, certain lipophilic organic acids have undesirable flavor and or aroma characteristics which would preclude their presence as the sole organic acid (e.g., in equimolar or greater quantities relative to nicotine). Without wishing to be bound by theory, it is believed that a combination of different organic acids may provide the desired ion pairing while the concentration of any single organic acid in the composition remains below the threshold which would be found objectionable from a sensory perspective.

For example, in some embodiments, the organic acid may comprise from about 1 to about 5 or more molar equivalents of benzoic acid relative to nicotine, combined with e.g., about 0.2 molar equivalents of octanoic acid acid or a salt thereof, and 0.2 molar equivalents of decanoic acid or a salt thereof.

In some embodiments, the organic acid is a combination of any two organic acids selected from the group consisting of benzoic acid, a toluic acid, benzenesulfonic acid, toluenesulfonic acid, hexanoic acid, heptanoic acid, decanoic acid, and octanoic acid. In some embodiments, the organic acid is a combination of benzoic acid, octanoic acid, and decanoic acid, or benzoic and octanoic acid. In some embodiments, the composition comprises citric acid in addition to one or more of benzoic acid, a toluic acid, benzenesulfonic acid, toluenesulfonic acid, hexanoic acid, heptanoic acid, decanoic acid, and octanoic acid.

In some embodiments, the composition comprises an alkali metal salt of an organic acid. For example, at least a portion of the organic acid may be present in the composition in the form of an alkali metal salt. Suitable alkali metal salts include lithium, sodium, and potassium. In some embodiments, the alkali metal is sodium or potassium. In some embodiments, the alkali metal is sodium. In some embodiments, the composition comprises an organic acid and a sodium salt of the organic acid.

In some embodiments, the composition comprises benzoic acid and sodium benzoate, octanoic acid and sodium octanoate, decanoic acid and sodium decanoate, or a combination thereof.

In some embodiments, the ratio of the organic acid to the sodium salt of the organic acid is from about 0.1 to about 10, such as from about 0.1, about 0.25, about 0.3, about 0.5, about 0.75, or about 1, to about 2, about 5, or about 10. For example, in some embodiments, both an organic acid and the sodium salt thereof are added to the other components of the composition, wherein the organic acid is added in excess of the sodium salt, in equimolar quantities with the sodium salt, or as a fraction of the sodium salt. One of skill in the art will recognize that the relative amounts will be determined by the desired pH of the composition, as well as the desired ionic strength. For example, the organic acid may be added in a quantity to provide a desired pH level of the composition, while the alkali metal (e.g., sodium) salt is added in a quantity to provide the desired extent of ion pairing. As one of skill in the art will understand, the quantity of organic acid (i.e., the protonated form) present in the composition, relative to the alkali metal salt or conjugate base form present in the composition, will vary according to the pH of the composition and the pKa of the organic acid, as well as according to the actual relative quantities initially added to the composition.

The amount of organic acid or an alkali metal salt thereof present in the composition, relative to nicotine, may vary. Generally, as the concentration of the organic acid (or the conjugate base thereof) increases, the percent of nicotine that is ion paired with the organic acid increases. This typically increases the partitioning of the nicotine, in the form of an ion pair, into octanol versus water as measured by the logP (the logio of the partitioning coefficient). In some embodiments, the composition comprises from about 0.05, about 0.1, about 1, about 1.5, about 2, or about 5, to about 10, about 15, or about 20 molar equivalents of the organic acid, the alkali metal salt thereof, or the combination thereof, relative to the nicotine component, calculated as free base nicotine.

In some embodiments, the composition comprises from about 2 to about 10, or from about 2 to about 5 molar equivalents of the organic acid, the alkali metal salt thereof, or the combination thereof, to nicotine, on a free-base nicotine basis. In some embodiments, the organic acid, the alkali metal salt thereof, or the combination thereof, is present in a molar ratio with the nicotine from about 2, about 3, about 4, or about 5, to about 6, about 7, about 8, about 9, or about 10. In embodiments wherein more than one organic acid, alkali metal salt thereof, or both, are present, it is to be understood that such molar ratios reflect the totality of the organic acids present.

In certain embodiments the organic acid inclusion is sufficient to provide a composition pH of from about 4.0 to about 9.0, such as from about 4.5 to about 7.0, or from about 5.5 to about 7.0, from about 4.0 to about 5.5, or from about 7.0 to about 9.0. In some embodiments, the organic acid inclusion is sufficient to provide a composition pH of from about 4.5 to about 6.5, for example, from about 4.5, about 5.0, or about 5.5, to about 6.0, or about 6.5. In some embodiments, the organic acid is provided in a quantity sufficient to provide a pH of the composition of from about 5.5 to about 6.5, for example, from about 5.5, about 5.6, about 5.7, about 5.8, about 5.9, or about 6.0, to about 6.1, about 6.2, about 6.3, about 6.4, or about 6.5. In other embodiments, a mineral acid (e.g., hydrochloric acid, sulfuric acid, phosphoric acid, or the like) is added to adjust the pH of the composition to the desired value.

In some embodiments, the organic acid is added as the free acid, either neat (i.e., native solid or liquid form) or as a solution in, e.g., water, to the other composition components. In some embodiments, the alkali metal salt of the organic acid is added, either neat or as a solution in, e.g., water, to the other composition components. In some embodiments, the organic acid and the basic amine (e.g., nicotine) are combined to form a salt, either before addition to the composition, or the salt is formed within and is present in the composition as such. In other embodiments, the organic acid and basic amine (e.g., nicotine) are present as individual components in the composition, and form an ion pair upon contact with moisture (e.g., saliva in the mouth of the consumer).

Basic Amine

The composition as disclosed herein comprises a basic amine. By "basic amine" is meant a molecule including at least one basic amine functional group. Examples of basic amines include, but are not limited to, alkaloids. By "basic amine functional group" is meant a group containing a nitrogen atom having a lone pair of electrons. The basic amine functional group is attached to or incorporated within the molecule through one or more covalent bonds to the said nitrogen atom. The basic amine may be a primary, secondary, or tertiary amine, meaning the nitrogen bears one, two, or three covalent bonds to carbon atoms. By virtue of the lone pair of electrons on the nitrogen atom, such amines are termed "basic", meaning the lone electron pair is available for hydrogen bonding. The basicity (i.e., the electron density on the nitrogen atom and consequently the availability and strength of hydrogen bonding to the nitrogen atom) of the basic amine may be influenced by the nature of neighboring atoms, the steric bulk of the molecule, and the like.

Generally, the basic amine is released from the composition and absorbed through the oral mucosa, thereby entering the blood stream, where it is circulated systemically.

Generally, the basic amine is present in or as an active ingredient in the composition, as described herein below. In some embodiments, the basic amine is nicotine or a nicotine component. By "nicotine component" is meant any suitable form of nicotine (e.g., free base, salt, or ion pair) for providing oral absorption of at least a portion of the nicotine present. Nicotine is released from the composition and absorbed through the oral mucosa, thereby entering the blood stream, where it is circulated systemically.

Typically, the nicotine component is selected from the group consisting of nicotine free base, nicotine as an ion pair, and a nicotine salt. In some embodiments, at least a portion of the nicotine is in its free base form. In some embodiments, at least a portion of the nicotine is present as a nicotine salt, or at least a portion of the nicotine is present as an ion pair with at least a portion of the organic acid or the conjugate base thereof, as disclosed herein above.

Typically, the nicotine component (calculated as the free base) is present in a concentration of at least about 0.001% by weight of the composition, such as in a range from about 0.001% to about 10%. In some embodiments, the nicotine component is present in a concentration from about 0.1% w/w to about 10% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about from about 0.1% w/w to about 2.5%, from about 0.1% to about 2.0%, from about 0.1% to about 1.5%, or from about 0.1% to about 1% by weight, calculated as the free base and based on the total weight of the composition.

Filler

The compositions as described herein comprise one or more fillers. Fillers may fulfill multiple functions, such as enhancing certain organoleptic properties such as texture and mouthfeel, enhancing cohesiveness or compressibility of the product, and the like.

Generally, fillers are porous particulate materials and are cellulose-based. For example, suitable fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the mixture based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "modified" starches. Other starches are obtained and subsequently modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, enzyme treatment, acetylation, hydroxypropylation, and/or partial hydrolysis. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, starch sodium octenyl succinate.

Additional examples of potential fillers include maltodextrin, dextrose, calcium carbonate, calcium phosphate, lactose, and sugar alcohols. Combinations of fillers can also be used. In some embodiments, the filler comprises or is a mixture of glucose and starch-derived polysaccharides. One such suitable mixture of glucose and starch-derived polysaccharides is EMDEX®, available from JRS PHARMA LP, USA, 2981 Route 22, Patterson, NY 12563-2359.

In some embodiments, the particulate filler is a cellulose material or cellulose derivative. One particularly suitable particulate filler for use in the compositions described herein is microcrystalline cellulose ("mcc"). The mcc may be synthetic or semi-synthetic, or it may be obtained entirely from natural celluloses. The mcc may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. In one embodiment, the composition comprises mcc as the particulate filler. The quantity of mcc present may vary according to the desired properties.

The amount of filler can vary, but is typically up to about 75 percent of the composition by weight, based on the total weight of the composition. A typical range of filler (e.g., mcc) within the composition can be from about 10 to about 75 percent by total weight of the composition, for example, from about 10, about 15, about 20, about 25, or about 30, to about 35, about 40, about 45, or about 50 weight percent (e.g., about 20 to about 50 weight percent or about 25 to about 45 weight percent). In certain embodiments, the amount of filler is at least about 10 percent by weight, such as at least about 20 percent, or at least about 25 percent, or at least about 30 percent, or at least about 35 percent, or at least about 40 percent, based on the total weight of the composition.

In one embodiment, the filler further comprises a cellulose derivative or a combination of such derivatives. In some embodiments, the composition comprises from about 1 to about 10% of the cellulose derivative by weight, based on the total weight of the composition, with certain embodiments comprising about 1 to about 5% by weight of cellulose derivative. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives methylcellulose, include hydroxypropylcellulose ("HPC"), hydroxypropylmethylcellulose ("HPMC"), hydroxyethyl cellulose, and carboxymethylcellulose ("CMC"). In one embodiment, the cellulose derivative is one or more of methylcellulose, HPC, HPMC, hydroxyethyl cellulose, and CMC. In one embodiment, the cellulose derivative is HPC.

In some embodiments, the composition comprises from about 1 to about 3% HPC by weight, based on the total weight of the composition.

Water

The water content of the composition, prior to use by a consumer of the composition, may vary according to the desired properties. Typically, the composition is less than about 60 percent by weight of water, and generally is from about 1 to about 60% by weight of water, for example, from about 5 to about 55, about 10 to about 50, about 20 to about 45, or about 25 to about 40 percent water by weight, including water amounts of at least about 5% by weight, at least about 10% by weight, at least about 15% by weight, and at least about 20% by weight.

Active Ingredient

The composition as disclosed herein, in certain embodiments, comprises an active ingredient. As used herein, an "active ingredient" refers to one or more substances belonging to any of the following categories: API (active pharmaceutical substances), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, and/or pharmaceutical, nutraceutical, and medicinal ingredients (e.g., vitamins, such as B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular product.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species).

When present, a botanical is typically at a concentration of from about 0.01% w/w to about 10% by weight, such as, e.g., from about from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include ashwagandha, Bacopa monniera, baobab, basil, *Centella asiatica*, Chai-hu, chamomile, cherry blossom, chlorophyll, cinnamon, citrus, cloves, cocoa, *cordyceps*, curcumin, damiana, *Dorstenia arifolia, Dorstenia odorata*, essential oils, *eucalyptus*, fennel, *Galphimia glauca*, ginger, *Ginkgo biloba, ginseng* (e.g., *Panax ginseng*), green tea, *Griffonia simplicifolia*, guarana, hemp, hops, jasmine, *Kae-*

*mpferia parviflora* (Thai *ginseng*), kava, lavender, lemon balm, lemongrass, licorice, lutein, maca, matcha, *Nardostachys chinensis*, oil-based extract of *Viola odorata*, peppermint, quercetin, resveratrol, *Rhizoma gastrodiae, Rhodiola*, rooibos, rose essential oil, rosemary, Sceletium *tortuosum*, Schisandra, Skullcap, spearmint extract, Spikenard, terpenes, tisanes, turmeric, *Turnera aphrodisiaca*, valerian, white mulberry, and Yerba mate.

Stimulants

In some embodiments, the active ingredient comprises one or more stimulants. As used herein, the term “stimulant” refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are “natural” stimulants. By “naturally derived” is meant the stimulant (e.g., caffeine, theacrine) is in a purified form, outside its natural (e.g., botanical) matrix. For example, caffeine can be obtained by extraction and purification from botanical sources (e.g., tea). By “wholly synthetic”, it is meant that the stimulant has been obtained by chemical synthesis. In some embodiments, the active ingredient comprises caffeine. In some embodiments, the active ingredient is caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

Amino Acids

In some embodiments, the active ingredient comprises an amino acid. As used herein, the term “amino acid” refers to an organic compound that contains amine (—$NH_2$) and carboxyl (—COOH) or sulfonic acid ($SO_3H$) functional groups, along with a side chain (R group), which is specific to each amino acid. Amino acids may be proteinogenic or non-proteinogenic. By “proteinogenic” is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By “non-proteinogenic” is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine.

When present, an amino acid or combination of amino acids (e.g., taurine, theanine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

Vitamins

In some embodiments, the active ingredient comprises a vitamin or combination of vitamins. As used herein, the term “vitamin” refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones).

When present, a vitamin or combination of vitamins (e.g., vitamin B6, vitamin B12, vitamin E, vitamin C, or a combination thereof) is typically at a concentration of from about 0.01% w/w to about 1% by weight, such as, e.g., from about from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, or about 1% by weight, based on the total weight of the composition.

Cannabinoids

In some embodiments, the active ingredient comprises one or more cannabinoids. As used herein, the term “cannabinoid” refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in *cannabis*; and synthetic cannabinoids, manufactured artificially. Non-limiting examples of cannabinoids include tetrahydrocannabinol (THC), the primary psychoactive compound in *cannabis*, and cannabidiol (CBD) another major constituent of the plant, but which is devoid of psychoactivity. In some embodiments, the active ingredient comprises CBD.

When present, a cannabinoid (e.g., CBD) is typically in a concentration of at least about 0.1% by weight of the composition, such as in a range from about 0.1% to about 30%, such as, e.g., from about from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the composition.

Antioxidants

In some embodiments, the active ingredient comprises one or more antioxidants. As used herein, the term “antioxidant” refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, *ginseng*, gingko *biloba*, Saint John's Wort, saw palmetto, green tea, black tea, black cohosh, cayenne, chamomile, cloves, cocoa powder, cranberry, dandelion, grapefruit, honeybush, *echinacea*, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, *papaya*, pennyroyal, peppermint, red clover, rooibos (red or green), rosehip, rosemary, sage, clary sage, savory, spearmint, *spirulina*, slippery elm bark, sorghum bran hi-tannin, sorghum grain hi-tannin, sumac bran, comfrey leaf and root, goji berries, gutu kola, thyme, turmeric, uva *ursi*, valerian, wild yam root, wintergreen, yacon root, yellow dock, yerba mate, yerba santa, bacopa monniera, withania somnifera, Lion's mane, and *Silybum marianum*. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl) propanoic acid), phosphatidylserine, myoinositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine.

When present, the amount of API may vary. For example, when present, an API is typically at a concentration of from about 0.001% w/w to about 10% by weight, such as, e.g., from about from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the composition.

As described herein above, the basic amine present in the composition may be nicotine or a nicotine component, or may be an active ingredient or a component of an active ingredient. One of skill in the art will recognize that many active ingredients as defined herein are comprised of molecules which may be categorized as basic amines. Accordingly, the ion pairing of such basic amine-containing active ingredients with the lipophilic organic acids as described herein are contemplated. In such embodiments, the ion pair of the active ingredient and organic acid, alkali metal salt of the organic acid, or combination thereof may enhance the stability of the composition comprising the ion pair, or enhance a predicted oral mucosal absorption of the active ingredient by virtue of the presence of the ion paired form of the active ingredient.

Flavoring Agent

In some embodiments, the composition as described herein comprises a flavoring agent. As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, *eucalyptus*, lavender, cardamom, nutmeg, cinnamon, clove, cascarilla, sandalwood, honey, jasmine, ginger, anise, sage, licorice, lemon, orange, apple, peach, lime, cherry, strawberry, pineapple, and any combinations thereof. See also, Leffingwell et al., Tobacco Flavoring for Smoking Products, R. J. Reynolds Tobacco Company (1972), which is incorporated herein by reference. Flavorings also may include components that are considered moistening, cooling or smoothening agents, such as *eucalyptus*. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; US Pat. App. Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The flavoring agent generally comprises at least one volatile flavor component. As used herein, "volatile" refers to a chemical substance that forms a vapor readily at ambient temperatures (i.e., a chemical substance that has a high vapor pressure at a given temperature relative to a nonvolatile substance). Typically, a volatile flavor component has a molecular weight below about 400 Da, and often include at least one carbon-carbon double bond, carbon-oxygen double bond, or both. In one embodiment, the at least one volatile flavor component comprises one or more alcohols, aldehydes, aromatic hydrocarbons, ketones, esters, terpenes, terpenoids, or a combination thereof. Non-limiting examples of aldehydes include vanillin, ethyl vanillin, p-anisaldehyde, hexanal, furfural, isovaleraldehyde, cuminaldehyde, benzaldehyde, and citronellal. Non-limiting examples of ketones include 1-hydroxy-2-propanone and 2-hydroxy-3-methyl-2-cyclopentenone-1-one. Non-limiting examples of esters include allyl hexanoate, ethyl heptanoate, ethyl hexanoate, isoamyl acetate, and 3-methylbutyl acetate. Non-limiting examples of terpenes include sabinene, limonene, gamma-terpinene, beta-farnesene, nerolidol, thujone, myrcene, geraniol, nerol, citronellol, linalool, and eucalyptol. In one embodiment, the at least one volatile flavor component comprises one or more of ethyl vanillin, cinnamaldehyde, sabinene, limonene, gamma-terpinene, beta-farnesene, or citral.

The amount of flavoring agent utilized in the composition can vary, but is typically up to about 10 weight percent, and certain embodiments are characterized by a flavoring agent content of at least about 0.1 weight percent, such as about 0.5 to about 10 weight percent, about 1 to about 6 weight percent, or about 2 to about 5 weight percent, based on the total weight of the composition. The amount of flavoring agent present within the composition may vary over a period of time (e.g., during a period of storage after preparation of the composition). For example, certain volatile components present in the composition may evaporate or undergo chemical transformations, leading to a reduction in the concentration of one or more volatile flavor components.

Taste Modifiers

In order to improve the organoleptic properties of a composition as disclosed herein, the composition may include one or more taste modifying agents ("taste modifiers") which may serve to mask, alter, block, or improve e.g., the flavor of a composition as described herein. Non-limiting examples of such taste modifiers include analgesic or anesthetic herbs, spices, and flavors which produce a perceived cooling (e.g., menthol, *eucalyptus*, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the composition comprises an active ingredient having a bitter taste, and a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., an active ingredient). Suitable taste modifiers include, but are not limited to, capsaicin, gamma-amino butyric acid (GABA), adenosine monophosphate (AMP), lactisole, or a combination thereof.

When present, a representative amount of taste modifier is about 0.01% by weight or more, about 0.1% by weight or more, or about 1.0% by weight or more, but will typically make up less than about 10% by weight of the total weight of the composition, (e.g., from about 0.01%, about 0.05%, about 0.1%, or about 0.5%, to about 1%, about 5%, or about 10% by weight of the total weight of the composition).

Salts

In some embodiments, the composition may further comprise a salt (e.g., alkali metal salts), typically employed in an amount sufficient to provide desired sensory attributes to the composition. Non-limiting examples of suitable salts include sodium chloride, potassium chloride, ammonium chloride, flour salt, and the like.

When present, a representative amount of salt is about 0.5 percent by weight or more, about 1.0 percent by weight or more, or at about 1.5 percent by weight or more, but will typically make up about 10 percent or less of the total weight of the composition, or about 7.5 percent or less or about 5 percent or less (e.g., about 0.5 to about 5 percent by weight).

Sweeteners

In order to improve the sensory properties of the composition according to the disclosure, one or more sweeteners may be added. The sweeteners can be any sweetener or combination of sweeteners, in natural or artificial form, or as a combination of natural and artificial sweeteners. Examples of natural sweeteners include fructose, sucrose, glucose, maltose, mannose, galactose, lactose, *stevia*, honey, and the like. Examples of artificial sweeteners include sucralose, isomaltulose, maltodextrin, saccharin, aspartame, acesulfame K, neotame, and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). In some embodiments, the sweetener is sucralose, acesulfame K, or a combination thereof.

When present, a sweetener or combination of sweeteners may make up from about 0.01 to about 20% or more of the of the composition by weight, for example, from about 0.01 to about 0.1, from about 0.1 to about 1%, from about 1 to about 5%, from about 5 to about 10%, or from about 10 to about 20% by weight, based on the total weight of the composition. In some embodiments, a combination of sweeteners is present at a concentration of from about 0.01% to about 0.1% by weight of the composition, such as about 0.01, about 0.02, about 0.03, about 0.04, about 0.05, about 0.06, about 0.07, about 0.08, about 0.09, or about 0.1% by weight of the composition. In some embodiments, a combination of sweeteners is present at a concentration of from about 0.1% to about 0.5% by weight of the composition, such as about 0.1, about 0.2, about 0.3, about 0.4, or about 0.5% by weight of the composition. In some embodiments, a combination of sweeteners is present at a concentration of from about 1% to about 3% by weight of the composition.

Binding Agents

A binder (or combination of binders) may be employed in certain embodiments. Typical binders can be organic or inorganic, or a combination thereof. Representative binders include povidone, sodium alginate, starch-based binders, pectin, carrageenan, pullulan, zein, and the like, and combinations thereof. A binder may be employed in amounts sufficient to provide the desired physical attributes and physical integrity to the composition. The amount of binder utilized in the composition can vary, but is typically up to about 30 weight percent, and certain embodiments are characterized by a binder content of at least about 0.1% by weight, such as about 1 to about 30% by weight, or about 5 to about 10% by weight, based on the total weight of the composition.

Other suitable binders include a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the composition.

Humectants

In certain embodiments, one or more humectants may be employed in the composition. Examples of humectants include, but are not limited to, glycerin, propylene glycol, and the like. Where included, the humectant is typically provided in an amount sufficient to provide desired moisture attributes to the composition. Further, in some instances, the humectant may impart desirable flow characteristics to the composition for depositing in a mold.

When present, a humectant will typically make up about 5% or less of the weight of the composition (e.g., from about 0.5 to about 5% by weight). When present, a representative amount of humectant is about 0.1% to about 1% by weight, or about 1% to about 5% by weight, based on the total weight of the composition.

Buffering Agents

In certain embodiments, the composition of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Non-limiting examples of suitable buffers include alkali metals acetates, glycinates, phosphates, glycerophosphates, citrates, carbonates, hydrogen carbonates, borates, or mixtures thereof.

Where present, the buffering agent is typically present in an amount less than about 5 percent based on the weight of the composition, for example, from about 0.5% to about 5%, such as, e.g., from about 0.75% to about 4%, from about 0.75% to about 3%, or from about 1% to about 2% by weight, based on the total weight of the composition.

Colorants

A colorant may be employed in amounts sufficient to provide the desired physical attributes to the composition. Examples of colorants include various dyes and pigments, such as caramel coloring and titanium dioxide. Natural colorants such as curcumin, beet juice extract, *spirulina*; also a variety of synthetic pigments may also be used. The amount of colorant utilized in the composition can vary, but when present is typically up to about 3% by weight, such as from about 0.1%, about 0.5%, or about 1%, to about 3% by weight, based on the total weight of the composition.

Tobacco Material

In some embodiments, the composition may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata*, N. x sanderae, *N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. *Hersperis, N. pauciflora, N. petunioides, N. quadrivalvis, N. repanda, N. rotundifolia, N. solanifolia*, and *N. spegazzinii*. Various representative other types of plants from the *Nicotiana* species are set forth in Goodspeed, The Genus *Nicotiana*, (Chonica Botanica) (1954); U.S. Pat. No. 4,660,577 to Sensabaugh, Jr. et al.; 5,387,416 to White et al., U.S. Pat. No. 7,025,066 to Lawson et al.; U.S. Pat. No. 7,798,153 to Lawrence, Jr. and 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; 5,387,416 to White et al.; and 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the mixture most preferably includes tobacco lamina, or a tobacco lamina and stem mixture (of which at least a portion is smoke-treated). Portions of the tobaccos within the mixture may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the d mixture optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral compositions, it is typical for a harvested plant of the *Nicotiana* species to be subjected to a curing process. The tobacco materials incorporated within the composition as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.,* 21, 305-320 (2005) and Staaf et al., *Beitrage Tabakforsch. Int.,* 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in US Pat. Pub. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art.

For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; 9,420,825 to Beeson et al.; and 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and 7,337,782 to Thompson, all of which are incorporated by reference herein.

Typical inclusion ranges for tobacco materials can vary depending on the nature and type of the tobacco material, and the intended effect on the final mixture, with an example range of up to about 30% by weight (or up to about 20% by weight or up to about 10% by weight or up to about 5% by weight), based on total weight of the composition (e.g., about 0.1 to about 15% by weight). In some embodiments, the compositions of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or 0% by weight of tobacco material.

Oral Care Additives

In some embodiments, the composition comprises an oral care ingredient (or mixture of such ingredients). Oral care ingredients provide the ability to inhibit tooth decay or loss, inhibit gum disease, relieve mouth pain, whiten teeth, or otherwise inhibit tooth staining, elicit salivary stimulation, inhibit breath malodor, freshen breath, or the like. For example, effective amounts of ingredients such as thyme oil, *eucalyptus* oil and zinc (e.g., such as the ingredients of formulations commercially available as ZYTEX® from Discus Dental) can be incorporated into the composition. Other examples of ingredients that can be incorporated in desired effective amounts within the present composition can include those that are incorporated within the types of oral care compositions set forth in Takahashi et al., *Oral Microbiology and Immunology,* 19 (1), 61-64 (2004); U.S. Pat. No. 6,083,527 to Thistle; and US Pat. Appl. Pub. Nos. 2006/0210488 to Jakubowski and 2006/02228308 to Cummins et al. Other exemplary ingredients of tobacco containing-formulation include those contained in formulations marketed as MALTISORB® by Roquette and DENTIZYME® by NatraRx. When present, a representative amount of oral care additive is at least about 1%, often at least about 3%, and frequently at least about 5% of the total dry weight of the composition. The amount of oral care additive within the composition will not typically exceed about 30%, often will not exceed about 25%, and frequently will not exceed about 20%, of the total dry weight of the composition.

Processing Aids

If necessary for downstream processing of the composition, such as granulation, mixing, or molding, a flow aid can also be added to the composition in order to enhance flowability of the composition. In some embodiments, the composition (e.g., melt and chew forms) may be surface treated with anti-stick agents, such as oils, silicones, and the like. Exemplary flow aids include microcrystalline cellulose, silica, polyethylene glycol, stearic acid, calcium stearate, magnesium stearate, zinc stearate, sodium stearyl fumarate, carnauba wax, and combinations thereof. In some embodiments, the flow aid is sodium stearyl fumarate.

When present, a representative amount of flow aid may make up at least about 0.5 percent or at least about 1 percent, of the total dry weight of the composition. Preferably, the amount of flow aid within the composition will not exceed about 5 percent, and frequently will not exceed about 3 percent, of the total dry weight of the composition.

Other Additives

Other additives can be included in the disclosed composition. For example, the composition can be processed, blended, formulated, combined and/or mixed with other materials or ingredients. The additives can be artificial, or can be obtained or derived from herbal or biological sources. Examples of further types of additives include thickening or gelling agents (e.g., fish gelatin), emulsifiers, preservatives (e.g., potassium sorbate and the like), disintegration aids, or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference.

Typical inclusion ranges for such additional additives can vary depending on the nature and function of the additive and the intended effect on the final composition, with an example range of up to about 10% by weight, based on total weight of the composition (e.g., about 0.1 to about 5% by weight).

The aforementioned additives can be employed together (e.g., as additive formulations) or separately (e.g., individual additive components can be added at different stages involved in the preparation of the final mixture). Furthermore, the aforementioned types of additives may be encapsulated as provided in the final product or composition. Example encapsulated additives are described, for example, in WO2010/132444 to Atchley, which has been previously incorporated by reference herein.

Particulate

In some embodiments, any one or more of the filler, tobacco material, other composition components, and the overall composition described herein can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, the column of sieves may be placed on or in a mechanical agitator. The agitator causes the vibration of each of the sieves in the column. The mechanical agitator may be activated for a pre-determined period of time in order to ensure that all particles are collected in the correct sieve. In some embodiments, the column of sieves is agitated for a period of time from 0.5 minutes to 10 minutes, such as from 1 minute to 10 minutes, such as from 1 minute to 5 minutes, such as for approximately 3 minutes. Once the agitation of the sieves in the column is complete, the material collected on each sieve is weighed. The weight of each sample on each sieve may then be divided by the total weight in order to obtain a percentage of the mass retained on each sieve. As the skilled person will readily appreciate, the screen opening sizes or mesh sizes for each sieve in the column used for sieve analysis may be selected based on the granularity or known maximum/minimum particle sizes of the sample to be analysed. In some embodiments, a column of sieves may be used for sieve analysis, wherein the column comprises from 2 to 20 sieves, such as from 5 to 15 sieves. In some embodiments, a column of sieves may be used for sieve analysis, wherein the column comprises 10 sieves. In some embodiments, the largest screen opening or mesh sizes of the sieves used for sieve analysis may be 1000 μm, such as 500 μm, such as 400 μm, such as 300 μm.

In some embodiments, any particulate material referenced herein (e.g., filler, tobacco material, and the overall composition) can be characterized as having at least 50% by weight of particles with a particle size as measured by sieve analysis of no greater than about 1000 μm, such as no greater than about 500 μm, such as no greater than about 400 μm, such as no greater than about 350 μm, such as no greater than about 300 μm. In some embodiments, at least 60% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 70% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 80% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 90% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 95% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, at least 99% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm. In some embodiments, approximately 100% by weight of the particles of any particulate material referenced herein have a particle size as measured by sieve analysis of no greater than about 1000 μm, such as no greater than about 500 μm, such as no greater than about 400 μm, such as no greater than about 350 μm, such as no greater than about 300 μm.

In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 0.01 μm to about 1000 μm, such as from about 0.05 μm to about 750 μm, such as from about 0.1 μm to about 500 μm, such as from about 0.25 μm to about 500 μm. In some embodiments, at least 50% by weight, such as at least 60% by weight, such as at least 70% by weight, such as at least 80% by weight, such as at least 90% by weight, such as at least 95% by weight, such as at least 99% by weight of the particles of any particulate material referenced herein have a particle size as measured by sieve analysis of from about 10 μm to about 400 μm, such as from about 50 μm to about 350 μm, such as from about 100 μm to about 350 μm, such as from about 200 μm to about 300 μm.

Preparation of the Composition

The manner by which the various components of the mixture are combined may vary. As such, the overall mixture of various components with e.g., powdered mixture components may be relatively uniform in nature. The components noted above, which may be in liquid or dry solid form, can be admixed in a pretreatment step prior to mixture with any remaining components of the mixture, or simply mixed together with all other liquid or dry ingredients. The various components of the mixture may be contacted, combined, or mixed together using any mixing technique or equipment known in the art. Any mixing method that brings the mixture ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and 6,834,654 to Williams, each of which is incorporated herein by reference. In some embodiments, the components forming the mixture are prepared such that the mixture thereof may be used in a starch molding process for forming the mixture. Manners and methods for formulating mixtures will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and 6,077,524 to Bolder et al., each of which is incorporated herein by reference.

Configured for Oral Use

Provided herein is a composition configured for oral use. The term "configured for oral use" as used herein means that the composition is provided in a form such that during use, saliva in the mouth of the user causes one or more of the components of the composition (e.g., basic amine, flavoring agents and/or active ingredients) to pass into the mouth of the user. In certain embodiments, the composition is adapted to deliver components to a user through mucous membranes in the user's mouth, the user's digestive system, or both, and, in some instances, said component is a nicotine component or an active ingredient (including, but not limited to, for example, nicotine, a stimulant, vitamin, amino acid, botanical, or a combination thereof) that can be absorbed through the mucous membranes in the mouth or absorbed through the digestive tract when the product is used.

Compositions configured for oral use as described herein may take various forms, including gels, pastilles, gums, chews, melts, tablets, lozenges, powders, and pouches. Gels can be soft or hard. Certain compositions configured for oral use are in the form of pastilles. As used herein, the term "pastille" refers to a dissolvable oral composition made by solidifying a liquid or gel composition so that the final composition is a somewhat hardened solid gel. The rigidity of the gel is highly variable. Certain compositions of the disclosure are in the form of solids. Certain compositions can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The compositions as disclosed herein can be formed into a variety of shapes, including pills, tablets, spheres, strips, films, sheets, coins, cubes, beads, ovoids, obloids, cylinders, bean-shaped, sticks, or rods. Cross-sectional shapes of the composition can vary, and example cross-sectional shapes include circles, squares, ovals, rectangles, and the like. Such shapes can be formed in a variety of manners using equipment such as moving belts, nips, extruders, granulation devices, compaction devices, and the like.

The compositions of the present disclosure may be dissolvable. As used herein, the terms "dissolve," "dissolving," and "dissolvable" refer to compositions having aqueous-soluble components that interact with moisture in the oral cavity and enter into solution, thereby causing gradual consumption of the composition. According to one aspect, the dissolvable composition is capable of lasting in the user's mouth for a given period of time until it completely dissolves. Dissolution rates can vary over a wide range, from about 1 minute or less to about 60 minutes. For example, fast release compositions typically dissolve and/or release the desired component(s) (e.g., active ingredient, flavor, and the like) in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the composition. In other embodiments, the products do not dissolve during the product's residence in the user's mouth.

In some embodiments, the composition can be chewable, meaning the composition has a mild resilience or "bounce" upon chewing, and possesses a desirable degree of malleability. A composition in chewable form may be entirely dissolving, or may be in the form of a non-dissolving gum in which only certain components (e.g., active ingredients, flavor, sweetener) dissolve, leaving behind a non-dissolving matrix. Chewable embodiments generally include a binder, such as a natural gum or pectin. In some embodiments, the composition in chewable form comprises pectin and an organic acid, along with one or more sugar alcohols in an amount by weight of at least 50%, based on the total weight of the composition. Generally, the pectin is present in an amount of from about 1 to about 3% by weight, based on the total weight of the composition.

In some embodiments, the composition can be meltable as discussed, for example, in US Patent App. Pub. No. 2012/0037175 to Cantrell et al., incorporated by reference herein in its entirety. As used herein, "melt," "melting," and "meltable" refer to the ability of the composition to change from a solid state to a liquid state. That is, melting occurs when a substance (e.g., a composition as disclosed herein) changes from solid to liquid, usually by the application of heat. The application of heat in regard to a composition as disclosed herein is provided by the internal temperature of a user's mouth. Thus, the term "meltable" refers to a composition that is capable of liquefying in the mouth of the user as the composition changes phase from solid to liquid, and is intended to distinguish compositions that merely disintegrate in the oral cavity through loss of cohesiveness within the composition that merely dissolve in the oral cavity as aqueous-soluble components of the composition interact with moisture. Generally, meltable compositions comprise a lipid as described herein above. In some embodiments, the composition in meltable form comprises a lipid in an amount of from about 35 to about 50% by weight, based on the total weight of the composition, and a sugar alcohol in an amount of from about 35 to about 55% by weight, based on the total weight of the composition. In some embodiments, the sugar alcohol is isomalt, erythritol, sorbitol, arabitol, ribitol, maltitol, dulcitol, iditol, mannitol, xylitol, lactitol, or a combination thereof. In some embodiments, the sugar alcohol is isomalt.

In certain embodiments, the composition is in the form of a compressed or molded pellet. Example pellet weights range from about 250 mg to about 1500 mg, such as about 250 mg to about 700 mg, or from about 700 mg to about 1500 mg. The pellet can have any of a variety of shapes, including traditional pill or tablet shapes. Generally, the composition in tablet form comprises a glucose-polysaccharide blend and a sugar alcohol. In some embodiments, the glucose-polysaccharide blend is present in an amount of from about 35 to about 50% by weight, based on the total weight of the composition; and the sugar alcohol is present in an amount of from about 30 to about 45% by weight, based on the total weight of the composition. In some embodiments, the sugar alcohol is isomalt, erythritol, sorbitol, arabitol, ribitol, maltitol, dulcitol, iditol, mannitol, xylitol, lactitol, or a combination thereof. In some embodiments, the sugar alcohol is isomalt.

In one embodiment, the composition of the present disclosure is disposed within a moisture-permeable container (e.g., a water-permeable pouch). Such compositions in the water-permeable pouch format are typically used by placing one pouch containing the mixture in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the composition therein (e.g., flavoring agents and/or nicotine) to pass through e.g., the water-permeable pouch and provide the user with flavor and satisfaction, and the user is not required to spit out any portion of the mixture. After about 10 minutes to about 60 minutes, typically about 15 minutes to about 45 minutes, of use/enjoyment, substantial amounts of the mixture have been ingested by the human subject, and the pouch may be removed from the mouth of the human subject for disposal.

Accordingly, in certain embodiments, the composition as disclosed herein and any other components noted above are combined within a moisture-permeable packet or pouch that acts as a container for use of the composition to provide a pouched product configured for oral use. Certain embodiments of the disclosure will be described with reference to FIG. 1 of the accompanying drawings, and these described embodiments involve snus-type products having an outer pouch and containing a mixture as described herein. As explained in greater detail below, such embodiments are provided by way of example only, and the pouched products of the present disclosure can include the composition in other forms. The mixture/construction of such packets or pouches, such as the container pouch 102 in the embodiment illustrated in FIG. 1, may be varied. Referring to FIG. 1, there is shown a first embodiment of a pouched product 100. The pouched product 100 includes a moisture-permeable container in the form of a pouch 102, which contains a material 104 comprising a composition as described herein.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The mixture may be contained in pouches and packaged, in a manner and using the types of components used for the manufacture of conventional snus types of products. The pouch provides a liquid-permeable container of a type that may be considered to be similar in character to the mesh-like type of material that is used for the construction of a tea bag. Components of the mixture readily diffuse through the pouch and into the mouth of the user.

Non-limiting examples of suitable types of pouches are set forth in, for example, U.S. Pat. No. 5,167,244 to Kjerstad and 8,931,493 to Sebastian et al.; as well as US Patent App. Pub. Nos. 2016/0000140 to Sebastian et al.; 2016/0073689 to Sebastian et al.; 2016/0157515 to Chapman et al.; and 2016/0192703 to Sebastian et al., each of which are incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and mixture each may undergo complete dispersion within the mouth of the user during normal conditions of use, and hence the pouch and mixture both may be ingested by the user. Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the mixture contents permeate through the pouch material prior to the time that the pouch undergoes loss of its physical integrity. If desired, flavoring ingredients, disintegration aids, and other desired components, may be incorporated within, or applied to, the pouch material.

The amount of material contained within each product unit, for example, a pouch, may vary. In some embodiments, the weight of the mixture within each pouch is at least about 50 mg, for example, from about 50 mg to about 1 gram, from about 100 to 800 about mg, or from about 200 to about 700 mg. In some smaller embodiments, the weight of the mixture within each pouch may be from about 100 to about 300 mg. For a larger embodiment, the weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887,307 to Scott et al. and 6,923,981 to Leung et al.; and The EFSA Journal (2004) 85, 1-32; which are incorporated herein by reference.

A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference.

Storage and Storage Period

Compositions of the present disclosure configured for oral use (e.g., in pouched form) may be packaged and stored in any suitable packaging in much the same manner that conventional types of smokeless tobacco products are packaged and stored. For example, a plurality of packets or pouches may be contained in a cylindrical container. The storage period of the product after preparation may vary. As used herein, "storage period" refers to the period of time after the preparation of the disclosed product. In some embodiments, one or more of the characteristics of the products disclosed herein (e.g., lack of color change, retention of volatile flavor components, retention of nicotine) is exhibited over some or all of the storage period. In some embodiments, the storage period (i.e., the time period after preparation) is at least one day. In some embodiments, the storage period is from about 1 day, about 2 days, or about 3 days, to about 1 week, or from about 1 week to about 2 weeks, from about 2 weeks to about 1 month, or from about 1 month to about 2 months, about 3 months, about 4 months, about 5 months, or about 6 months. In some embodiments, the storage period is any number of days between about 1 and about 180. In certain embodiments, the storage period may be longer than 6 months, for example, about 7 months, about 8 months, about 9 months, about 10 months, about 11 months, about 12 months, about 18 months, or about 24 months.

Method of Enhancing Stability

In another aspect is provided a method of enhancing the stability of a composition configured for oral use as disclosed herein. In some embodiments, the method comprises mixing the at least one filler with the water, the basic amine, and the organic acid, the alkali metal salt of an organic acid, or the combination thereof to form the composition, wherein at least a portion of the basic amine is associated with at least a portion of the organic acid or the alkali metal salt thereof, the association in the form of a basic amine-organic acid salt, an ion pair between the basic amine and a conjugate base of the organic acid, or both, wherein the composition has a pH of less than about 8. In some embodiments, the basic amine is nicotine.

In some embodiments, the method further comprises adding a solubility enhancer to the composition.

In some embodiments, the method further comprises adjusting the pH of the composition to a pH less than about 7.0. In some embodiments, adjusting the pH comprises adding an organic acid to the composition, providing the pH of less than about 7.0. In some embodiments, adjusting the pH comprises adding a mineral acid to the composition, providing the pH of less than about 7.0. In some embodiments, adjusting the pH comprises adding both an organic acid and a mineral acid to the composition, providing the pH of less than about 7.0.

In some embodiments, enhancing the stability comprises reducing the evaporative loss of basic amine (e.g., nicotine) from the composition over a storage period, relative to a composition configured for oral use which has a pH of greater than about 8.

In some embodiments, the storage period is one or more of 1 month, 2 months, 3 months, 4 months, 5 months, or 6 months after preparation. In some embodiments, the loss of basic amine (e.g., nicotine) is less than about 5% after a storage period of 6 months. In some embodiments, the storage period is greater than 6, greater than 12, greater than 18 or even greater than 24 months.

Method of Enhancing a Predicted Oral Absorption

In a further aspect is provided a method of enhancing a predicted oral (e.g., buccal) absorption of a basic amine (e.g., nicotine) from a composition configured for oral use as disclosed herein. While obtaining actual absorption data requires invasive experiments, predictive data may be readily obtained through use of buccal membrane permeability in vitro. For example, percent permeation of nicotine through such a membrane, or permeation versus time, may be evaluated and compared for various embodiment of nicotine-containing oral compositions. For example, oral compositions according to the disclosure may be compared against control compositions (e.g., nicotine in the absence of an organic acid, nicotine in the presence of an organic acid having a logP of less than 1.4, etc.), providing surrogate data predictive of actual buccal absorption.

In some embodiments, the method of enhancing a predicted oral absorption comprises mixing the at least one filler with the water, the basic amine, and the organic acid, the alkali metal salt of an organic acid, or the combination thereof to form the composition, wherein at least a portion of the basic amine is associated with at least a portion of the organic acid or the alkali metal salt thereof, the association in the form of a basic amine-organic acid salt, an ion pair between the basic amine and a conjugate base of the organic acid, or both.

In some embodiments, the method further comprises adding a solubility enhancer to the composition.

In some embodiments, the method further comprises adjusting the pH of the composition to a pH of from about 4.0 to about 7.0. In some embodiments, adjusting the pH comprises adding an organic acid to the composition, providing the pH of from about 4.0 to about 7.0. In some embodiments, adjusting the pH comprises adding a mineral acid to the composition, providing the pH of from about 4.0 to about 7.0. In some embodiments, adjusting the pH comprises adding both an organic acid and a mineral acid to the composition, providing the pH of from about 4.0 to about 7.0.

In some embodiments, enhancing the predicted oral absorption comprises increasing the total basic amine % permeated relative to a composition comprising an organic acid, an alkali metal salt of an organic acid, or a combination thereof, wherein the organic acid has a logP value of less than about 1.4.

In some embodiments, the basic amine is nicotine, In some embodiments, enhancing the predicted oral absorption comprises increasing the total nicotine % permeated relative to a composition comprising an organic acid, an alkali metal salt of an organic acid, or a combination thereof, wherein the organic acid has a logP value of less than about 1.4.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

Aspects of the present invention are more fully illustrated by the following examples, which are set forth to illustrate certain aspects of the present invention and are not to be construed as limiting thereof.

Example 1. Calculation of Free Nicotine as a Function of pH

The Henderson-Hasselbalch equation ($pH=pK_a+\log 10 (A-/HA)$) was used to calculate the percentage of free nicotine present in solution at different pH values. The data provided in Table 2 demonstrate that the proportion of free nicotine changes drastically as the pH changes around the $pK_a$ of nicotine.

TABLE 2

Free nicotine as a function of pH calculated from the Henderson-Hasselbalch equation using a $pK_a$ of 8.02.

| pH | free nicotine (%) |
|---|---|
| 8.5 | 75.1 |
| 8 | 48.8 |
| 7.5 | 23.2 |
| 7 | 8.7 |
| 6.5 | 2.9 |

Example 2. Calculated Nicotine Partitioning at pH 8.4

The theoretical octanol-water partitioning of a pH 8.4 nicotine solution was calculated based on partitioning coefficients obtained from Molinspiration software (https://www.molinspiration.com/services/logp.html). The values utilized were log(P)=1.09 for free nicotine and log(P)=−2.07 for protonated nicotine. The percent protonation at calculated the Henderson-Hasselbalch equation (Table 3). The calculation indicates that at pH 8.4, approximately 65% of the total nicotine available is expected to be present in the octanol layer.

TABLE 3

Calculated Percent Nicotine in Octanol and Water at pH 8.4

| Parameter | Free Nic | Nic $H^+$ |
|---|---|---|
| Nicotine species distribution @ pH 8.4 (Henderson-Hasselbalch) %: | 70.58 | 29.42 |
| Log(P) | 1.09 | −2.07 |
| P | 12.303 | 0.008511 |
| Nicotine Species in Water (%) | 5.31 | 29.17 |
| Nicotine Species in Octanol (%) | 65.27 | 0.25 |
| Total Nicotine Species in Octanol (%) | 65.52 | |

Example 3. Nicotine Octanol-Water Partitioning at 100 ppm and pH 5

A solution of nicotine (1000 ppm; 6.17 mM) was prepared by adding free base nicotine (0.2 grams) to a volumetric flask (200 mL) and filling to volume with reverse osmosis (RO) purified water. Individual 6.17 mM solutions of trisodium citrate, sodium benzoate, sodium heptanesulfonate, monosodium tartrate, and sodium levulinate were prepared. Aliquots of the nicotine solution (10 mL), RO water (60 mL), and the respective citrate, benzoate, heptanesulfonate, tartrate, and levulinate solutions (10 mL) were added to tared Erlenmeyer flasks (125 mL), along with a control which did not contain any counterion. A pH probe was submerged in the resulting liquid and HCl (0.05 M) was added under stirring to bring the solution to pH 5. The flask weight was then brought up to 100 grams with RO water. The resulting solutions contained 1000 ppm nicotine with 1 molar equivalent of the respective sodium salt at a pH of 5. Partitioning was performed by removing aliquots (10 mL) of each solution and placing into separate 20 ml scintillation vials. Octanol (10 ml) was added to each vial. The vials were then placed on a wrist action shaker for 20 minutes. Following agitation, the vials were allowed to separate for 30 min, and an aliquot (100 μl) of each octanol layer was removed and diluted with 900 μl octanol in 2 mL GC/MS vials. The nicotine concentration of each sample was analyzed via GC/MS. The nicotine levels are provided in FIG. 2, which demonstrated an increase in octanol-water partitioning moving from the control and polar citric (logP=−1.7), tartaric (, and levulinic ( ) to more lipophilic acids such as heptanesulfonic acid (log(P)=0.88) and benzoic (log(P)=1.9). Without wishing to be bound by theory, it is believed this partitioning was the result of ion pair formation, with the ion pair exhibiting sufficient lipophilicity to effectively partition into octanol for the benzoic and heptanesulfonic acid samples. Notably, at this acidic pH and low concentration of nicotine and counterion, the overall partitioning for all the samples was very low (i.e., (1.2-8.5%). Again without wishing to be bound by theory, it is believed that the extent of ion pairing at the pH value and at the low nicotine/counterion concentrations reduced the extent of potential ion pairing by shifting the equilibrium toward free ions.

Example 4. Nicotine Octanol-Water Partitioning at 1000 ppm and pH 6.5

A solution of nicotine (10,000 ppm; 61.7 mM) was prepared by adding free base nicotine (2 grams) to a volumetric flask (200 mL) and filling to volume with reverse osmosis (RO) purified water. Individual 123.2 mM solutions of trisodium citrate, sodium benzoate, and sodium octanoate were prepared. Aliquots of the nicotine solution (10 mL), RO water (60 mL), and the respective sodium citrate, benzoate, or octanoate solutions (10 mL) were added to tared Erlenmeyer flasks (125 mL). A pH probe was submerged in the resulting liquid and HCl (0.05 M) was added under stirring to bring the solution to pH 6.5. The flask weight was then brought up to 100 grams with RO water. The resulting solutions contained 1,000 ppm nicotine with 2 molar equivalents of the respective sodium salt at a pH of 6.5. Partitioning was performed by removing aliquots (10 mL) of each solution and placing into separate 20 ml scintillation vials. Octanol (10 ml) was added to each vial. The vials were then placed on a wrist action shaker for 20 minutes. Following agitation, the vials were allowed to separate for 30 min, and an aliquot (100 μl) of each octanol layer was removed and diluted with 900 μl octanol in 2 mL GC/MS vials. The nicotine concentration of each sample was analyzed via GC/MS. The nicotine levels are provided in FIG. 3, which demonstrated an increase in octanol-water partitioning at pH 6.5 moving from the polar citric acid (log(P)=−1.7), to more lipophilic acids such as benzoic (log(P)=1.9) and octanoic acid (log(P)=3.0). Particularly, with 2 equivalents of octanoic acid present, a large portion (~67%) of the nicotine partitioned into octanol. Without wishing to be bound by theory, it is believed this partitioning was the result of ion pair formation, with the ion pair exhibiting sufficient lipophilicity to effectively partition into octanol.

Example 5. Nicotine and Benzoic Acid Octanol-Water Partitioning in Unbuffered Water A solution of 1000 ppm nicotine in unbuffered water containing 1 molar equivalent of sodium benzoate was prepared. This nicotine concentration was selected as equivalent to a pouched composition containing 6 mg of nicotine dissolving into 6 mL of saliva. The sample was subjected to octanol-water partitioning and analyzed for nicotine using the method of Example 2. The sample was also analyzed for benzoic acid concentration in octanol (100 μl aliquot diluted in 900 μl octanol). The benzoic acid concentration was measured using an HPLC-UV procedure adapted from the literature (Phenomenex, Application I.D. 14720). The separation was performed on a Luna 5m C18 column (150×3 mm; Phenomenex; Torrance, CA, USA), using a mobile phase with the following composition: $H_2O$ 75%, $CH_3CN$ 25% containing 0.2 mM $KH_2PO_4$. The mobile phase was brought to pH 2.5 with $H_3PO_4$. The flow rate of the mobile phase was 1 mL/min, and the injection volume was 10 μL. The eluate was monitored at 254 nm. For the quantitation of the samples, a stock solution containing 260 ppm benzoic acid in $H_2O$ was initially made. This solution was diluted to make standard solutions at 260, 130, 65, 32.5, and 16.25 μg/mL respectively. The peak area obtained from these samples vs. concentration gave the following calibration line: $y=0.2573x+0.0372$, $R^2=0.9999$.

The concentrations in octanol were found to be 28.3 ppm for nicotine and 19.2 ppm for benzoic acid. The benzoic acid molarity in terms of nicotine mass was calculated to be 25.5 ppm nicotine. Accordingly, 90% (25.5/28.3) of the nicotine was partitioned in octanol due to benzoic acid and 2.8% (28.3-25.5) of the total nicotine was partitioned into octanol due to the propensity of free nicotine to partition into octanol (FIG. 4). In theory, nicotine and benzoic acid partitioning into octanol as an ion pair, would result in the presence of nicotine and benzoic acid in the octanol at a 1:1 molar ratio, reflecting the proposed stoichiometry of the ion pair. However, it was found in this experiment that the concentration of nicotine in octanol relative to benzoic acid was slightly higher than theory 28.3 vs 25.5 ppm). Without wishing to be bound by theory, it is believed that the larger concentration of nicotine in octanol was due to the natural partitioning of nicotine into octanol at pH of 6.5 (i.e., at pH 6.5, some of the nicotine is available as the free base, and partitions without depending on ion pairing). This data further supports the theory that changes in octanol-water partitioning are due to the presence of an ion pair, and not merely due to changes in system properties (such as modified solution polarity or formation of micelles).

Example 6. Reference (Control) Composition

A reference sample of a composition comprising 6 mg nicotine, microcrystalline cellulose (mcc), water, and additional components as disclosed herein (salt, binder, sweetener, humectant, flavorant) was prepared with no organic acid (pH ca. 9).

Example 7. Reference Composition (Citric Acid)

A reference sample of a composition comprising 6 mg nicotine, microcrystalline cellulose (mcc), water, and additional components as disclosed herein (salt, binder, sweetener, humectant, flavorant) was prepared containing 0.34% citric acid (pH ca. 6.5). Other than the presence of citric acid, the components and relative amounts of each component were essentially the same for Example 6.

Example 8. Octanol-Water Partitioning of Examples 6 and 7

Samples of each of the pouch fillers of Examples 6 and 7 (697.6 mg total, 10 mg nicotine) were precisely weighed into separate 20 mL scintillation vials. Partitioning was performed by adding to the samples water (10 mL; purified by reversis osmosis), followed by octanol (10 mL). The vials were then placed on a wrist action shaker for 2 hours. Following agitation, the vials were allowed to separate for 30 min, and an aliquot (100 μl) of each octanol layer was removed and diluted with octanol (900 μl) in 2 mL GC/MS vials. To each GC/MS vial was added 50 μL of a quinoline standard (1000 ppm in MeOH). The samples were run in triplicate, along with nicotine standards. The nicotine standards were prepared in octanol at 100, 50, 25, 12.5, 6.25, and 3.125 ppm. GC-MS analysis was performed according to standard methods. Results are provided in FIG. 5, which demonstrated that approximately 80% of the nicotine partitioned into the octanol, while only about 10% of the nicotine partitioned into the octanol for the citric acid containing example.

Example 9. Comparison of Nicotine Partitioning with Various Ion Pairing Agents & Quantities-Benzoate, Octanoate, and Decanoate A solution of nicotine (10,000 ppm; 61.7 mM) was prepared by adding free base nicotine (2 grams) to a volumetric flask (200 mL) and filling to volume with reverse osmosis (RO) purified water. Individual solutions of sodium benzoate, sodium octanoate, and sodium decanoate were prepared (0.62, 1.23, 3.08, 6.16, and 12.33 mmol). Aliquots of the nicotine solution (10 mL), RO water (60 mL), and the respective benzoate, octanoate, or decanoate solutions (10 mL) were added to tared Erlenmeyer flasks (125 mL). A pH probe was submerged in the resulting liquid and HCl (0.05 M) was added under stirring to bring the solution to pH 6.5. The flask weight was then brought up to 100 grams with RO water. The resulting solutions contained 1,000 ppm nicotine (equivalent to a pouched composition containing 6 mg of nicotine dissolving into 6 mL of saliva) with 1, 2, 5, 10, or 20 molar equivalents of the respective sodium salt at a pH of 6.5. Partitioning was performed by removing aliquots (10 mL) of each solution and placing into separate 20 ml scintillation vials. Octanol (10 ml) was added to each vial. The vials were then placed on a wrist action shaker for 20 minutes. Following agitation, the vials were allowed to separate for 30 min, and an aliquot (100 μl) of each octanol layer was removed and diluted with 900 μl octanol in 2 mL GC/MS vials. The nicotine concentration of each sample was analyzed via GC/MS. The nicotine levels are provided in FIG. 6, which demonstrated that the type of acid used significantly influenced the octanol-water partitioning of the respective ion pair. Specifically, for each concentration, the more lipophilic octanoic acid provided greater partitioning of nicotine into octanol relative to the more polar benzoic acid. Samples containing decanoic acid were prone to becoming soapy during the vigorous mixing necessary to perform the partitioning experiments. This was likely due to micelle formation, and resulted in partitioning data which were less reliable. Further, the soapy nature of the aqueous solutions precluded accurate pH adjustment; accordingly, data points at 2, 10, and 20 eq were excluded from FIG. 6.

The data in FIG. 6 further demonstrated that the extent of ion-pairing, and thus octanol-water partitioning, was dependent on concentration. For each of benzoic acid and octanoic acid, partitioning increased with acid concentration, reaching an apparent plateau for benzoic acid of approximately 20 equivalents (suggesting the maximal degree of ion pairing was achieved), consistent with theory. According to theory, as the number of equivalents of acid increases, the equilibrium of ion-paired to non-ion paired nicotine plus organic acid shifts to predominantly ion-paired. The data further demonstrated that there may be an upper limit to the lipophilicity for acids useful in an aqueous system. For instance, decanoic acid (log(P)=4.09) was shown to partition into octanol to an extent less than that expected by theory. This may have been due to the limited solubility of decanoic acid in water, or the formation of micelles, consistent with the "soapy" nature of the decanoic acid containing solutions.

Surprisingly, at the same pH, each of the benzoic and octanoic acid compositions displayed different partitioning behavior. The % nicotine in octanol partitioning was highest for the non-polar acid (octanoic acid; logP ~3, ~75% nicotine in octanol with 10 eq. octanoic acid). Partitioning of the benzoic acid example (benzoic acid logP ~1.85) at the same concentration was somewhat lower (~52% nicotine in octanol). Each of the Examples at pH 6.5 had lower partitioning of nicotine into octanol than Example 6 (79%; pH ~9), but much higher than Example 7 (10%; polar citric acid; log(P)=−1.7; pH 6.5). However, nicotine partitioning of the octanoic acid example at 2 equivalents was approximately the same as predicted for nicotine at pH 8.4 (65%; theoretical calculation from Henderson-Haselbach equation and LogP). This result indicates that surprisingly, the composition with octanoic acid was able to achieve equivalent partitioning of nicotine at a pH of 6.5 to that of nicotine alone at a pH of 8.4. Without wishing to be bound by theory, it is believed that ion pairing between nicotine and the relatively non-polar octanoic acid promoted the partitioning behavior. This demonstrates that it is possible to obtain an acidic composition which is therefore stabilized with respect to nicotine evaporation and decomposition, and which also has octanol-water partitioning consistent with that of nicotine at a higher pH. Such data is predictive of favorable oral absorption of nicotine for embodiments including a relatively non-polar organic acid.

Example 10. Reference Pouched Product (Control)

A reference (control) composition comprising 10 mg nicotine, microcrystalline cellulose (mcc), water, and additional components as disclosed herein (salt, sodium bicarbonate, binder, sweetener, humectant, flavorant) was prepared with no organic acid (pH ca. 8.4) was prepared and placed in a pouch. The pouched product was packaged in a standard flex-lid canister with side seal and stored at room temperature (20-25° C.).

Example 11. Pouched Product (Reference)

A reference composition comprising 10 mg nicotine, microcrystalline cellulose (mcc), water, and additional components as disclosed herein (salt, binder, sweetener, humectant, flavorant) was prepared with citric acid (approximately 0.6% by weight; pH ca. 6.7) and placed in a pouch. The pouched product was packaged in a standard flex-lid canister with side seal and stored at room temperature (20-25° C.).

Example 12. Pouched Product (Inventive)

An inventive composition comprising 10 mg nicotine, microcrystalline cellulose (mcc), water, and additional components as disclosed herein (salt, binder, sweetener, humectant, flavorant) were prepared using a combination of 2.4% benzoic, 0.11% octanoic, and 0.13% decanoic acid by weight, along with about 2.4% sodium benzoate (pH ca. 6.4) was prepared and placed in a pouch. The pouched product was packaged in a standard flex-lid canister with side seal and stored at room temperature (20-25° C.). Other than the presence of the acid components, the components and relative amounts of each component were essentially the same for Examples 10-12.

Example 13. Nicotine Stability and Volatilization Study

The products of Examples 10, 11, and 12 were analyzed for nicotine, moisture content, and pH immediately after preparation, at 3 months, and at 6 months of time from preparation (T0, T3 months, and T6, respectively). To assess volatility as a function of pH in these samples, nicotine data was calculated on a dry-weight basis to account for moisture volatilization and compared to original nicotine concentration. The results provided in Table 4 demonstrated that up to 13% of the nicotine was lost on storage for the control (Example 10), while the original level of nicotine was substantially retained in both acidic compositions (Example 12 and reference Example 11).

TABLE 4

% Reduction in nicotine over time

| Example # | Time | pH | Moisture % | Nicotine (mg/g) | Dry weight basis Nic (mg/g) | Reduction (%) |
|---|---|---|---|---|---|---|
| 10 | T0 | 8.38 | 47.11 | 13.46 | 25.45 | 0.0% |
| (Control) | T3 | 8.22 | 45.87 | 12.20 | 22.54 | 11.4% |
| | T6 | 8.15 | 44.01 | 12.40 | 22.15 | 13.0% |
| 11 (Ref) | T0 | 6.67 | 47.61 | 14.67 | 28.00 | 0.0% |
| | T3 | 6.74 | 44.78 | 15.00 | 27.16 | 3.0% |
| | T6 | 6.59 | 43.26 | 15.90 | 28.02 | −0.1% |
| 12 | T0 | 6.37 | 48.49 | 14.62 | 28.38 | 0.0% |
| | T3 | 6.45 | 46.81 | 14.50 | 27.26 | 4.0% |
| | T6 | 6.58 | 44.78 | 15.70 | 28.43 | −0.2% |

Example 14. Buccal Permeation

To evaluate the true impact of ion-pairing on buccal absorption in a human subject, several pouched embodiments were prepared and evaluated in a buccal absorption model using a tissue-based permeation assay (EpiOral™; MatTek Labs).

A microcellulose (MCC) based pouch filler composition containing 6 mg nicotine water, and additional components as disclosed herein (salt, binder, sweetener, humectant, flavorant) was prepared.

A control composition (Example 14A) was prepared by adding sodium bicarbonate to the composition to provide a starting pH of ~9.25. A pouch was filled with the composition and over sprayed to a standard 700 mg pouch weight.

A reference composition (Example 14B) was prepared by adding 0.34% citric acid to the composition to provide a starting pH of ~6.5. A pouch was filled with the composition and over sprayed to a standard 700 mg pouch weight.

An inventive composition (Example 14C) was prepared by adding 0.63% benzoic acid and 1.08% sodium benzoate (2.26 eq total benzoate, 0.925 eq benzoic acid) to the composition to provide a starting pH of ~6.5. A pouch was filled with the composition and over sprayed to a standard 700 mg pouch weight.

The respective pouches were individually extracted with complete artificial saliva (CAS) at a concentration of 300 mg/mL. The CAS extracts were then evaluated for absorption using the EpiOral™ (buccal) permeation assay. The analysis consisted of a negative control (EpiOral™ unexposed), a vehicle control (CAS), and positive controls (caffeine, Triton X100). Tissues (0.6 $cm^2$) were exposed apically with donor solutions, and a receiver solution consisting of a PBS solution containing calcium, magnesium, and glucose was collected at four time points (15, 30, 45, and 60 minutes) for each sample. All analyses were performed in hexlicate (test articles) or triplicate (controls). Transepithelial electrical resistance was measured to verify tissue integrity at 0 minutes and at the final time point. Receiver and donor solutions were analyzed for analytes (nicotine and controls), and the resulting data was processed to give cumulative permeation, apparent rate of permeation ($P_{app}$), and percent recovery. Cumulative percent permeation was determined by quantifying overall mass permeated and dividing by tissue area. Apparent rate of permeation ($P_{app}$) was determined using Equation 2.

$$P_{app}=(dQ/dt)*(1/AC_0) \quad \text{(Equation 2)}$$

where (dQldt) is steady state flux, A is the area of cells (0.6 $cm^2$), and $C_0$ is the initial concentration applied to the apical side of the tissue. Percent recovery was determined by dividing the final donor solution concentration, receiver solution concentrations, and rinse solution concentrations (tissues were rinsed with CAS following receiver solution removal) by the initial donor solution concentrations.

The results for the assay are provided in FIGS. 7-9. FIG. 7 provides the % total permeated nicotine for Examples 14A, 14B, and 14C. Example 14A (control) demonstrated the highest nicotine permeation at 25%, while the reference Example 14B showed only about 5% permeation. The inventive Example 14C exhibited permeation between the reference and control examples, and correlated with the octanol-water partitioning experiment. Consistent with percent permeation, data for Papp followed the same trend (FIG. 8). Together, these data demonstrated that the polarity of the acid used for adjusting pH of the nicotine containing compositions significantly impacted the rate and total transfer through buccal tissue. Data in FIG. 9 confirmed that all of the nicotine present was recovered in the experiment.

What is claimed is:

1. A composition configured for oral use, the composition comprising:
- at least one filler;
- a basic amine;
- water; and
- an organic acid and a sodium or potassium salt of the organic acid;
- wherein the organic acid has a logP value of from 1.4 to 8.0, and
- at least a portion of the basic amine is associated with at least a portion of the organic acid or the sodium or potassium salt thereof, the association in the form of an ion pair between the basic amine and a conjugate base of the organic acid; and
- wherein a ratio of the organic acid to the sodium or potassium salt of the organic acid is from about 0.1 to about 10.

2. The composition of claim 1, wherein the organic acid has a logP value of from about 1.4 to about 4.5.

3. The composition of claim 1, wherein the organic acid has a logP value of from about 2.5 to about 3.5.

4. The composition of claim 1, wherein the organic acid has a logP value of from about 4.5 to about 8.0, and wherein the composition further comprises a solubility enhancer.

5. The composition of claim 4, wherein the solubility enhancer is glycerol or propylene glycol.

6. The composition of claim 1, comprising from about 0.05, about 0.1, about 1, about 1.5, about 2, or about 5, to about 10, about 15, or about 20 molar equivalents of the organic acid and the sodium or potassium salt thereof, relative to the basic amine, calculated as the amine free base.

7. The composition of claim 1, comprising from about 2 to about 10 molar equivalents of the organic acid and the sodium or potassium salt thereof, relative to the basic amine, calculated as the amine free base.

8. The composition of claim 1, wherein the organic acid is an alkyl carboxylic acid, an aryl carboxylic acid, an alkyl sulfonic acid, an aryl sulfonic acid, or a combination of any thereof.

9. The composition of claim 1, wherein the organic acid is octanoic acid, decanoic acid, benzoic acid, heptanesulfonic acid, or a combination thereof.

10. The composition of claim 1, wherein the organic acid is octanoic acid.

11. The composition of claim 1, comprising benzoic acid and sodium benzoate, octanoic acid and sodium octanoate, decanoic acid and sodium decanoate, or a combination thereof.

12. The composition of claim 1, wherein the pH of the composition is from about 4.0 to about 9.0.

13. The composition of claim 1, wherein the pH of the composition is from about 4.5 to about 7.

14. The composition of claim 1, wherein the pH of the composition is from about 5.5 to about 7.

15. The composition of claim 1, wherein the pH of the composition is from about 4.0 to about 5.5.

16. The composition of claim 1, wherein the pH of the composition is from about 7.0 to about 9.0.

17. The composition of claim 1, wherein the basic amine is nicotine.

18. The composition of claim 17, wherein the nicotine is present in an amount of from about 0.001 to about 10% by weight of the composition, calculated as the free base and based on the total weight of the composition.

19. The composition of claim 1, wherein the at least one filler comprises a cellulose material.

20. The composition of claim 19, wherein the cellulose material comprises microcrystalline cellulose.

21. The composition of claim 1, wherein the at least one filler further comprises a cellulose derivative in an amount by weight of from about 1% to about 3%, based on the total weight of the composition.

22. The composition of claim 21, wherein the cellulose derivative is hydroxypropylcellulose.

23. The composition of claim 1, comprising:

from about 10 to about 50% of the at least one filler; and from about 5 to about 60% by weight of water, based on the total weight of the composition.

24. The composition of claim 1, further comprising one or more active ingredients, one or more flavoring agents, one or more salts, one or more sweeteners, one or more binding agents, one or more humectants, one or more gums, a tobacco material, or combinations thereof.

25. The composition of claim 1, further comprising one or more active ingredients selected from the group consisting of nutraceuticals, botanicals, stimulants, amino acids, vitamins, and cannabinoids.

26. The composition of claim 1, comprising no more than about 10% by weight of a tobacco material, excluding any nicotine component present, based on the total weight of the composition.

27. The composition of claim 1, wherein the composition is free of tobacco material.

28. The composition of claim 1, enclosed in a pouch to form a pouched product, the composition optionally being in a granular form.

29. The composition of claim 1, comprising octanoic acid and sodium octanoate.

30. The composition of claim 1, comprising decanoic acid and sodium decanoate.

31. A method of enhancing the stability of a composition configured for oral use, the stabilized composition comprising:

at least one filler;

a basic amine;

water; and an organic acid and a sodium or potassium salt of the organic acid, wherein a ratio of the organic acid to the sodium or potassium salt of the organic acid is from about 0.1 to about 10;

wherein the organic acid has a logP value of from about 1.4 to about 8.0, the method comprising:

mixing the at least one filler with the water, the basic amine, the organic acid, and the sodium or potassium salt of the organic acid to form the composition, wherein at least a portion of the basic amine is associated with at least a portion of the organic acid or the sodium or potassium salt thereof, the association in the form of an ion pair between the basic amine and a conjugate base of the organic acid, wherein the composition has a pH of less than about 8.

32. The method of claim 31, wherein the organic acid has a logP value of from about 1.4 to about 4.5.

33. The method of claim 31, wherein the organic acid has a logP value of from about 2.5 to about 3.5.

34. The method of claim 31, wherein the organic acid has a logP value of from about 4.5 to about 8.0, and wherein the method further comprises adding a solubility enhancer to the composition.

35. The method of claim 31, further comprising adjusting the pH of the composition to a pH less than about 7.0, wherein adjusting the pH comprises adding an organic acid, a mineral acid, or both, to the composition, providing the pH of less than about 7.0.

36. The method of claim 31, wherein less than about 5% of an initial concentration of basic amine is lost after a storage period of 6 months.

37. The method of claim 36, wherein the basic amine is nicotine.

38. The method of claim 31, wherein the composition comprises from about 2 to about 20 molar equivalents of the organic acid and the sodium or potassium salt thereof, relative to the basic amine, calculated as the amine free base.

39. A method of enhancing a predicted oral mucosal absorption of a basic amine from a composition configured for oral use, the composition comprising:

at least one filler;

a basic amine;

water; and an organic acid and a sodium or potassium salt of the organic acid, wherein a ratio of the organic acid to the sodium or potassium salt of the organic acid is from about 0.1 to about 10;

wherein the organic acid has a logP value of from about 1.4 to about 8.0, the method comprising:

mixing the at least one filler with the water, the basic amine, the organic acid, and the sodium or potassium salt of the organic acid to form the composition, wherein at least a portion of the basic amine is associated with at least a portion of the organic acid or the sodium or potassium salt thereof, the association in the form of an ion pair between the basic amine and a conjugate base of the organic acid.

40. The method of claim 39, wherein the organic acid has a logP value of from about 1.4 to about 4.5.

41. The method of claim 39, wherein the organic acid has a logP value of from about 2.5 to about 3.5.

42. The method of claim 39, wherein the organic acid has a logP value of from about 4.5 to about 8.0, and wherein the method further comprises adding a solubility enhancer to the composition.

43. The method of claim 39, further comprising adjusting the pH of the composition to a pH from about 4.0 to about 7.0.

44. The method of claim 43, wherein adjusting the pH comprises adding a mineral acid to the composition.

45. The method of claim 39, wherein the basic amine is nicotine.

46. The method of claim 39, wherein the composition comprises from about 2 to about 20 molar equivalents of the organic acid and the sodium or potassium salt thereof, relative to the basic amine, calculated as the amine free base.

* * * * *